US008080640B2

(12) United States Patent
Funk et al.

(10) Patent No.: US 8,080,640 B2
(45) Date of Patent: *Dec. 20, 2011

(54) RECOMBINANT TRANSFERRINS, TRANSFERRIN HALF-MOLECULES AND MUTANTS THEREOF

(75) Inventors: Walter D. Funk, Dallas, TX (US); Robert C. Woodworth, Shelburne, VT (US); Anne B. Mason, Charlotte, VT (US); Ross T. A. MacGillivray, Vancouver (CA)

(73) Assignees: University of Vermont, Burlington, VT (US); The University of British Columbia, Vancouver (CA)

( * ) Notice: Subject to any disclaimer, the term of this patent is extended or adjusted under 35 U.S.C. 154(b) by 53 days.
This patent is subject to a terminal disclaimer.

(21) Appl. No.: 10/887,711

(22) Filed: Jul. 8, 2004

(65) Prior Publication Data

US 2005/0054043 A1   Mar. 10, 2005

Related U.S. Application Data

(63) Continuation of application No. 09/439,740, filed on Nov. 15, 1999, now Pat. No. 6,825,037, which is a continuation of application No. 08/175,158, filed on Dec. 28, 1993, now Pat. No. 5,986,067.

(51) Int. Cl.
*C12P 15/01* (2006.01)
*C12P 15/07* (2006.01)
*A61K 38/00* (2006.01)

(52) U.S. Cl. ............ 530/394; 530/350; 530/387.3; 435/440; 435/172.1; 424/278.1

(58) Field of Classification Search .......... 530/394; 435/440
See application file for complete search history.

(56) References Cited

U.S. PATENT DOCUMENTS 4,841,026 A * 6/1989 Van Beveren et al. ........ 530/394
5,026,651 A * 6/1991 Bowman et al. ............ 435/320.1

FOREIGN PATENT DOCUMENTS

EP   0 307 247   3/1989
EP   0 309 787   4/1989

OTHER PUBLICATIONS

Modun et al. (1998) Receptor-mediated recognition and uptake of iron from human transferrin by *Staphylococcus aureus* and *Staphylococcus epidermidis*. Infect. Immun. vol. 66, No. 8, pp. 3591-1596.*
Baumstark, J. S. (1987) A simple one-column procedure for the separation of swine and human serum transferrins, J. Biochem .Biophys. Methods, vol. 14, No. 2, pp. 59-70.*
Baldwin'et al. (1981) The effect of salts on the kinetics of iron release from N-terminal and C terminal monoferrictransferrins, Biochem. Biophys. Res. Commun, vol. 99, No. 4, pp. 1101-1107.*
Schaeffer et al. (1987) Complete structure of the human transferrin gene. Comparison with analogous chicken gene and human pseudogene, Gene, vol. 56, No. 1, pp. 109-116.*
He et al. (1996) Spectrophotometric titration with cobalt(III) for the determination of accurate absorption coefficients of transferrins, Biochem J., vol. 318, Part 1, pp. 145-148.*
Mason et al. (1992) Expression of glycosylated and nonglycosylated human transferrin in mammalian cells. Characterization of the recombinant proteins with comparison to three commercially available transferrins, Biochemistry, vol. 32, pp. 5472-5479.*
Woodworth et al. "Recombinant human transferrin N terminal half-molecule: characterization and NMR studies" *J. Cell Biochem.* Suppl 0 13(part A): 31 (1989).
Funk et al. "Expression of the amino terminal half molecule of human serum transferrin in cultured cells and characterization of the recombinant protein" *Biochemistry* 29: 1645-1660. (1990).
Woodworth et al. "Recombinant human transferrin amino-terminal half-molecule characterization of selectively deuterated and mutated proteins" *J. Cell. Biochem Suppl.* 0 (14 Part C) 1990. 204. (1990).
Adrian et al. "The human transferrin gene: 5' region contains conserved sequences which match the control elements regulated by heavy metals, glucocorticoids and acute phase reaction" *Gene.* 49:167-175 (1986).
Aldred et al. "Synthesis of rat transferrin in *Escherichia coli* containing a recombinant bacteriophage" *Biochem. Biophys. Res. Column.*, 122(3):960-965 (1984).
Baumstark "A simple one-column procedure for the separation of swine and human serum transferrins" *J. Biochem. Biophys. Methods* 14(2):59-70 (1987).
Brown-Mason et al. "Physiological Levels of Binding . . . " *Journal of Biol. Chem.* 259(3):1866-1873 (1984).
Clark-Lewis et al. "Automated Chemical Synthesis of a Protein Growth Factor for Hemopoietic Cells, Interleukin-3" *Science,* 231:134-139 (1986). Day et al. "Studies of the N-terminal half of human lactoferrin produced from the cloned cDNA demonstrate that interlobe interactions modulate iron release" *J. Bio. Chem.,* 267(20):13857-13862 (1992).
Fischbach "Expression of chimeric human transferrin genes in vitro" *J. Neuroscience Res.,* 27:633-641 (1990).
Funk et al. "Expression of the amino-terminal half-molecule of human serum transferrin in cultured cells and characterization of the recombinant protein" Biochem. 29:1654-1660 (1990).
Hershberger et al. "A cloned gene for human transferrin" *Annals New York Academy of Sciences,* 646:140-154 (1991).
Ill et al. "Species specificity of iron delivery in hybridomas" *In Vitro Cell. & Devel. Biol.,* 24:413-419 (1988).
Ikeda et al. "Production of human serum transferrin in *Escherichia coli" Gene.,* 117:265-269 (1992).
Jeltsch et al. "The complete nucleotide sequence . . . " *Eur. J. Biochem.,* 122:291-295 (1982).
Lineback-Zins et al. "Preparation and characterization of an $NH_2$-terminal fragment of human serum transferrin containing a single iron-binding site" *J. Biol. Chem.* 225(2):708-713 (1980).
MacGillivray et al. "The primary structure of human serum transferrin" *J. Biol. Chem.* 258(6):3543-3553 (1983).
Mason et al. "Efficient production and isolation of recombinant amino-terminal half-molecule of human serum transferrin from baby hamster kidney cells" *Protein Expression and Purification,* 2:214-220 (1991).

(Continued)

*Primary Examiner* — Anand Desai
*Assistant Examiner* — Samuel Liu
(74) *Attorney, Agent, or Firm* — Nelson Mullins Riley & Scarborough LLP; Debra J. Milasincic, Esq.

(57) ABSTRACT

Recombinant transferrin, non-glycosylated recombinant transferrin, transferrin half-molecules and mutant transferrins having altered metal-binding or other properties are described. The recombinant transferrin molecules are expressed in functional form by stable eukaryotic cell lines such as baby hamster kidney cells transformed with an expression vector encoding the recombinant molecule. The recombinant transferrins can be used in metal chelation therapy to bind and clear excess toxic metals in patients suffering from metal overloads or as tissue culture medium supplements or replacements.

24 Claims, 9 Drawing Sheets

OTHER PUBLICATIONS

Mason et al. "Expression of glycosylated and nonglycosylated human transferrin in mammalian cells. Characterization of the recombinant proteins with comparison to three commercially available transferrins" *Biochem.* 32:5472-5479 (1993).

McKnight et al. "Expression of the chicken transferrin gene in transgenic mice" Cell, *34:335-341* (1983).

Sigma Chemical Co., Catalog, p. 1177 (1986).

Stowell et al. "Expression of cloned human lactoferrin in baby-hamster kidney cells" *Biochem. J.*, 276:349-355 (1991).

Titeux et al. "The role of iron in the growth of human leukemic cell lines" *J. Cell. Physiol.*, 121:251-256 (1984).

Uzan et al. "Molecular cloning and sequence analysis of cDNA for human transferrin" *Biochem. Biophys. Res. Commun.* 119(1):273-281 (1984).

Wang et al. "Preliminary crystallographic analyses of the N-terminal lobe of recombinant human serum transferrin" *J. Mol. Biol.*, 227:575-576 (1992).

Woodworth et al. "Expression and initial characterization of five site-directed mutants of the N-terminal half-molecule of human transferrin" *Biochem.* (*Reprint*), 30:10824-10829 (1991).

Woodworth et al. "Recombinant human transferrin n-terminal half-molecule characterizations of selectively deuterated and mutated proteins" *UCLA Symposium: the Inorganic Chemistry/Molecular Biology Interface*, Feb. 24-Mar. 1, 1990.

Yang et al. "Human Transferrin: cDNA characterization and chromosomal localization" *Proc. Natl. Acad. Sci., USA*, 81:2752-2756 (1984).

Zak et al. "Preparation and properties of a single-sited fragment from the C-terminal domain of human transferrin" *Biochima et Biophysica Acta*, 829:348-353 (1985).

Rado et al. (1987) *Blood* 70(4): 989-993.

Kamboh, M.I. et al., "Human Transferrin Polymorphism," *Hum. Hered.*, vol. 37:65-81 (1987).

* cited by examiner

FIG. 3A
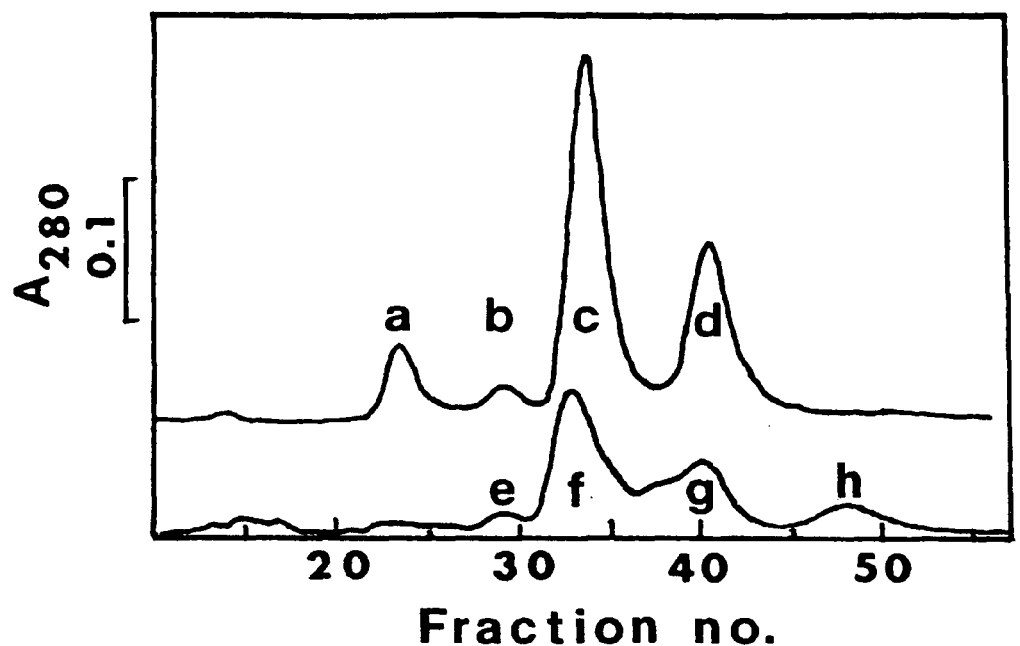
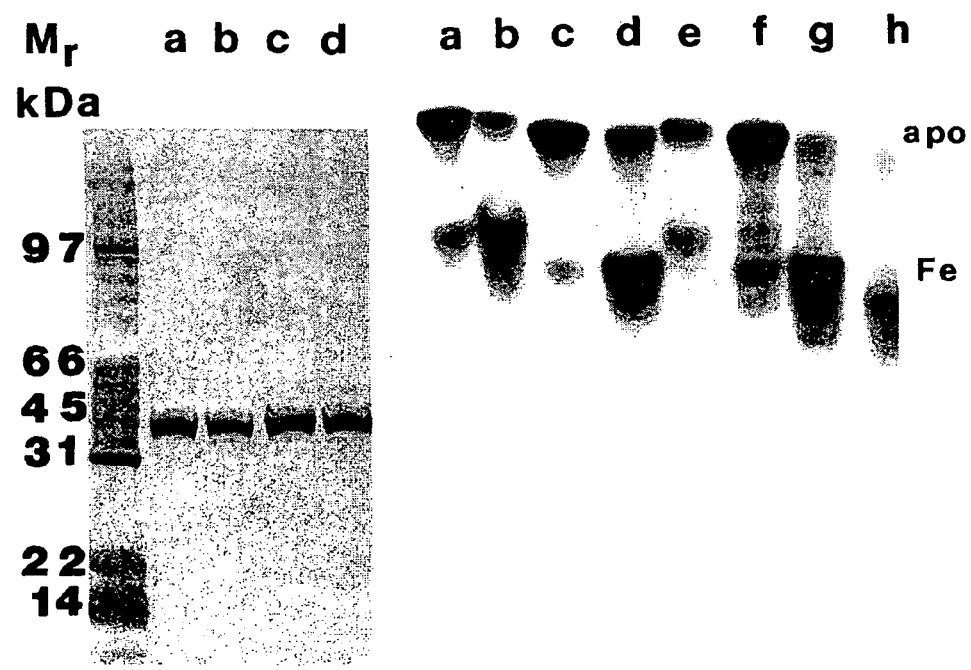
FIG. 3B
FIG. 3C

RECOMBINANT TRANSFERRINS, TRANSFERRIN HALF-MOLECULES AND MUTANTS THEREOF

RELATED APPLICATIONS

This application is a continuation of U.S. application Ser. No. 09/439,740, filed Nov. 15, 1999, which is now U.S. Pat. No. 6,825,037, which is a continuation of U.S. application Ser. No. 08/175,158, which is now U.S. Pat. No. 5,986,067, filed Dec. 28, 1993.

GOVERNMENT SUPPORT

This invention was made with government support under grant no. DK21739 awarded by the US Public Health Services (USPHS). The government has certain rights in the invention.

BACKGROUND OF THE INVENTION

The iron-binding pseudoglobulins collectively called transferrins or siderophilins comprise a class of proteins with strikingly similar features. X-ray crystallographic analyses of human lactoferrin (Anderson, B. F. et al. (1987) *Proc. Natl. Acad. Sci. USA* 84:1769-1773) and rabbit serum transferrin (Bailey, S. et al. (1988) *Biochemistry* 27:5804-5812) reveal that these proteins consist of two similar lobes connected by a short bridging peptide and that each lobe contains two domains defining a deep cleft containing the binding site for a metal ion and a synergistic anion.

The chicken ovotransferrin gene has been expressed in transgenic mice (McKnight, G. S. et al. (1983) *Cell* (Cambridge, Mass.) 34:335-341) and a fusion protein of part of rat transferrin with galactosidase has been expressed in *E. coli* (Aldred, A. et al. (1984) *Biochem. Biophys. Res. Commun.* 122:960-965). Except for this fusion protein, attempts to express transferrin or portions of the molecule in prokaryotic systems have been unsuccessful (Aldred, A. et al. (1984) *Biochem. Biophys. Res. Commun.* 122:960-965). The highly convoluted structure of the protein and large number of disulfide bridges in the molecule are probably the major impediments to expression in bacterial hosts. Attempts to mimic partially the natural protein folding environment by targeting the protein for bacterial membrane transport via an attached alkaline phosphatase signal sequence have been unsuccessful.

SUMMARY OF THE INVENTION

This invention pertains to recombinant transferrin, to recombinant transferrins that bind to the transferrin receptor, to recombinant transferrin half-molecules comprising at least the metal-binding domains of a single lobe (amino-terminal or carboxy-terminal) of transferrin and to stable cell culture system for expression of the transferrin. The recombinant transferrin can be expressed in stable, transformed eukaryotic cells, such as baby hamster kidney cells, to yield essentially homogeneous (monodisperse) preparations of the full or half-molecule forms. The invention also pertains to mutant transferrins, non-glycosylated transferrins and transferrin half-molecules which have metal-binding or other properties which are different from the natural (wild-type) form of the transferrin. These include mutant transferrins and transferrin half-molecules which bind iron or other metals more or less avidly than natural transferrin.

Transferrin half-molecules can be used in metal chelation therapy to treat individuals affected with abnormalities of metal regulation or with metal poisoning. For example, transferrin half-molecules, especially mutant forms which bind iron with a higher avidity than natural transferrin, can be administered to iron-overloaded individuals, e.g., thalassemics, in order to clear excess toxic iron from their bodies. In addition, half-molecules, or mutants thereof having altered metal ion selectivities, could be used to clear other toxic metals, e.g., lead, mercury, cadmium, copper and zinc from the body.

DESCRIPTION OF THE FIGURES

FIG. 3 shows the isolation and PAGE analysis of hTF/2N. (Panel A) FPLC isolations on a column of Polyanion SI of recombinant hTF/2N (upper trace) and proteolytically derived hTF/2N (lower trace). (Panel B) $NaDodSO_4$-PAGE (5-12% gradient of acrylamide) of molecular weight standards (lane Mr) and 3 μg of each of peaks a-d from panel A. (Panel C) Urea-PAGE under nonreducing conditions of the FPLC peaks a-d (recombinant hTF/2N species) and peaks e-h (proteolytically derived hTF/2N species) from panel A. The positions of the apo-protein (apo) and iron-bound protein (Fe) are indicated. The conditions used for FPLC are given under Materials and Methods. FPLC fractions were pooled as follows; peak a (fractions 23-27), peak b (28-31), peak c (32-38), peak d (39-45), peak e (28-31), peak f (32-36), peak g (38-44), and peak h (46-51).

DETAILED DESCRIPTION OF THE INVENTION

Figure 1:
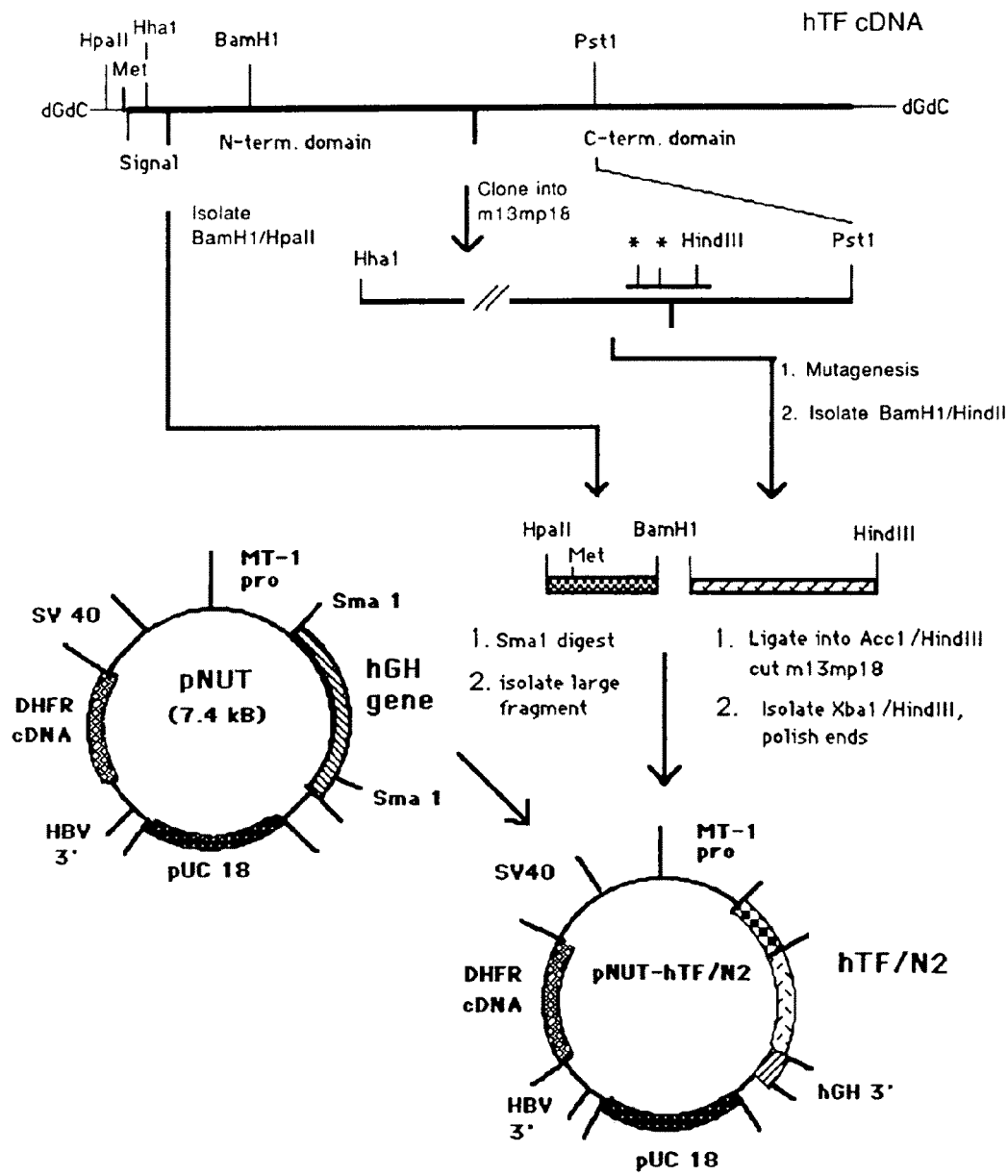
FIG. 1 shows construction of the hTF/2N expression vector in pNUT. A 2.3-kb cDNA encoding human serum transferrin was isolated from a human liver cDNA library and a 1.5-kb PstI/HaI fragment containing the complete amino-terminal domain coding sequence was cloned into M13mp18. Double translational stop codons and a HindIII recognition sequence were introduced by site-directed mutagenesis, allowing the isolation of a BamHI/HindIII fragment which, when joined to a BamHI/HpaII fragment, encodes the amino-terminal domain and signal sequence. This fragment was cloned into the eukaryotic expression vector pNUT, giving the vector pNUT-hTF/N2. In this plasmid, the transferrin cDNA is under the control of the metallothionein promoter (MT-1 pro) and the human growth hormone transcription termination signals (hGH3'); pNUT also contains the SV40 early promoter (SV40) driving expression of a resistant DHFR cDNA (DHFR cDNA) using transcription termination signals from human hepatitis B virus (HBV).

This invention provides for the production of recombinant transferrin, recombinant transferrin half-molecules and mutant forms of full-length transferrin and transferrin half-molecules which have altered properties, such as improved metal-binding capability, compared to the natural transferrin molecules. Recombinant transferrins can be produced in large quantities and in substantially homogeneous (monodisperse) form. For example, recombinant half-molecules of human serum transferrin can be produced as an essentially homogeneous preparation substantially free of other human serum proteins. In contrast, half-molecules prepared by proteolysis of the holo-protein are difficult to purify and, in fact, the carboxy-terminal half of human transferrin cannot be satisfactorily prepared by proteolytic means. Recombinant techniques also allow the application of mutagenesis to design and produce new forms of transferrin.

In general, a recombinant transferrin of this invention is produced by transfecting a suitable host cell with a nucleic acid construct encoding the transferrin, culturing the transfected host cell under conditions appropriate for expression and recovering the recombinant transferrin expressed by the cell. The amino acid sequences for eight transferrins have been reported (See S. S. Baldwin *Comp. Biochem Physiol.* 106b: 203-218 (1993)). The DNA sequence (SEQ ID NO: 1) and amino acid sequence (SEQ ID NO: 2) for human serum transferrin has been determined (Yang, F. et al. (1984) *Proc. Natl. Acad. Sci. USA* 81:2752-2756). Full-length DNA for production of recombinant transferrins or truncated DNA encoding either the amino-terminal or carboxy-terminal lobe of transferrin or a portion thereof can be obtained from available sources or can be synthesized according to the known sequences by standard procedures. In order to provide for secretion of the recombinant transferrin into cell culture medium, DNA encoding a transferrin signal sequence (or other signal sequence suitable for the expression system) is positioned upstream of the transferrin encoding DNA.

Through receptor-mediated endocytosis, cell-surface transferrin receptors deliver transferrin with its bound iron to peripheral endosomes where the iron is released into the cell and then the iron-free transferrin or apotransferrin is recycled to the extracellular fluid. Accordingly, another aspect of the invention is a homogenous preparation of human transferrin that is recognized by a transferrin receptor and is free of other human proteins.

Mutant forms of transferrin and transferrin half-molecules can be produced by standard techniques of site-directed mutagenesis. See Taylor et al. (1985) *Nucleic Acids Res.* 13; 8749-8764; Zoller, M. J. and Smith, M. (1983) *Meth. Enzymol* 100:458-500. In particular, mutagenesis can be used to produce mutant transferrins which have metal-binding properties that are different from natural transferrin. For example, mutants capable of binding iron more avidly than natural transferrin can be produced. To produce such mutants, metal-binding domains can be mutagenized to replace one or more amino acids involved in binding with different amino acids. In human serum transferrin, the amino acids which are ligands for metal chelation are shown below (the number beside the amino acid indicates the position of the amino acid residue in the primary sequence where the first valine of the mature protein is designated position 1)

| Amino terminal lobe (amino acids 1-337) | | Carboxy terminal lobe (amino acids 343-679) | |
|---|---|---|---|
| Aspartic acid | 63 | Aspartic acid | 392 |
| Tyrosine | 95 | Tyrosine | 426 |
| Tyrosine | 188 | Tyrosine | 517 |
| Histidine | 249 | Histidine | 584 |

In other types of transferrin, the numbering is different, but the ligands (amino acids) are the same.

Other regions of transferrin control binding and these too can be targeted for mutagenesis. These are usually positively charged amino acids such as lysine, histidine or arginine. For example, a mutant transferrin half-molecule which binds iron more avidly than natural transferrin can be produced by replacing the lysine residue at position 206 with glutamine (AAG→CAG) or by replacing the histidine residue at position 207 with glutamic acid (CAG→GAG).

Further, human serum transferrin contains two N-linked oligosaccharides at Asn-413 and Asn-611 corresponding to AAT and AAC, respectively. These glycosylation sites can be removed by changing the codons to GAT and GAC which correspond to aspartic acid using, for example, oligonucleotide-directed mutagenesis. Thus, a non-glycosylated transferrin can be produced recombinantly.

The transferrin-encoding DNA is cloned into a eukaryotic expression vector containing appropriate regulatory elements to direct expression of the DNA. A preferred eukaryotic expression vector is the plasmid pNUT described by Palmiter, R. D. et al. (1987) *Cell* 50:435-443. This plasmid contains the mouse metallothionein promoter which induces transcription of the transferrin encoding DNA in the presence of heavy metal and transcription termination signals of human growth hormone. In addition, pNUT contains dihydrofolate reductase gene under control of the SV40 early promoter with transcription termination signals from human hepatitis B virus to allow selection in cell culture. The gene encodes a mutant form of the enzyme which has a 270-fold lower affinity for the competitive inhibitor methotrexate. This allows for the immediate selection of transfected cells in very high concentrations (0.5 mM) of methotrexate and abrogates the need for a recipient cell line that is deficient in dihydrofolate reductase. pNUT also contains pUC18 derived sequences which allows it to be amplified in *E. coli* to provide sufficient amounts of the plasmid for transfection of recipient cells.

The expression vector containing the DNA encoding the transferrin is incorporated into an appropriate host cell. The preferred host cell is a eukaryotic cell which can be transformed with the vector to yield a stable cell line which expresses a functionally active transferrin construct. A particularly useful cell is the baby hamster kidney cell. Baby hamster kidney cells can be transfected with a vector carrying the DNA construct encoding a transferrin (such as the pNUT plasmid) to provide a stable cell culture system which expresses and secretes a functionally active transferrin (full or half-molecule). These cells are well-suited for economical, large scale growth and can be obtained from readily available sources.

Standard techniques, such as calcium phosphate coprecipitation or electroporation can be used to transfect the eukaryotic host cell with the vector. The cell is then cultured under conditions appropriate to induce expression of the transferrin. For example, baby hamster kidney cells transfected with the pNUT vector are stimulated to express the transferrin construct in the presence of heavy metals. Baby hamster kidney cells are preferably cultured in the medium Dulbecco's Modified Eagle's medium-Ham's F-12 nutrient mixture with the serum substitute ULTROSER-G™ (Gibco) (serum substitute) at about 1%.

After an appropriate culture period, the expressed and secreted transferrin can be recovered from the culture medium. Standard purification procedures can be employed to yield a substantially homogeneous preparation of the recombinant transferrin. In one embodiment, the transferrin in the culture medium is saturated with iron and then purified by anion exchange chromatography.

The recombinant transferrins of the invention can be used to chelate and clear iron or other toxic metals from the body. The customary approach to iron chelation in vivo has been to assess a wide variety of naturally-occurring siderophores of microbial origin and synthetic iron chelators for their physiological effects, primarily the ability to bind and clear iron from the body. Many such compounds have been studied with varying abilities to clear iron and often with unacceptable side effects (Pitt, C. G. et al. (1979) *J. Pharm. Exp. Therap.* 208: 12-18). As a result, the only iron chelator used for clearing excess iron from humans remains deferoxamine, a cyclic peptide from *Streptomyces pilosis*.

A preferred transferrin for iron chelation therapy is a mutant transferrin half-molecule which binds iron more avidly than natural transferrin. The use of a mutant half-molecule allows for more efficient chelation and removal of the metal. A particularly preferred mutant half-molecule is K206Q, described in the Exemplification below, which contains a glutamine rather than a lysine at position 206.

A transferrin half-molecule is advantageous because unlike the holo-proteins, it passes through the glomeruli of the kidney and is excreted in the urine, so that metal is not only chelated but also cleared from the body. Moreover, the single half-molecules do not bind to transferrin receptors on the membrane of tissue cells and therefore do not deliver iron to these tissues. Further, half-molecules of human transferrin would probably be recognized as "self" by the human body and therefore would not elicit an immunological response.

In addition, mutant half-molecules can be designed to have altered metal ion selectivities. The chelators could be used to clear other toxic metals from the body, e.g., lead, mercury, cadmium, and copper.

For chelation therapy, the recombinant transferrin is administered to a patient in amounts sufficient to chelate the metal and reduce circulating levels below toxic levels. Generally, it is administered in a physiologically acceptable vehicle, such as saline, by a parenteral route (typically intravenously).

Recombinant full-length human transferrin can be used in nonserum supplements or replacements for cell culture media. Transferrin is required for iron uptake by growing cells. The use of recombinant transferrin avoids the risk of contamination with, e.g., HIV or hepatitis virus associated with transferrin purified from human serum or prions from fetal bovine serum.

The invention is illustrated further by the following exemplification:

Exemplification

I. Production of Recombinant Transferrin Half-Molecule Comprising the Amino-Terminal Lobe.

Materials

T4 DNA ligase, DNA polymerase I (Klenow fragment) and T4 polynucleotide kinase were purchased from Pharmacia-PL Biochemicals. Restriction endonucleases were purchased from Pharmacia-PL Biochemicals and Bethesda Research Laboratories. Oligodeoxyribo-nucleotides were synthesized on an Applied Biosystems 380A DNA Synthesizer. Nitrocellulose filters were obtained from Schleicher and Schuell, $^{32}$P-labeled nucleotides from New England Nuclear, goat anti-human transferrin antiserum from the Sigma Chemical Company, formalin-fixed *Staphylococcus aureus* cells from Bethesda Research Laboratories, the Protoblot immunoscreening detection system from Promega, the oligonucleotide-directed mutagenesis kit from Amersham, Dulbecco's modified essential medium and fetal bovine serum from Gibco, and anti-human transferrin monoclonal antibody HTF-14 was from the Czechoslovakian Academy of Sciences. All other reagents were analytical grade or purer.

Methods

Isolation of Human Serum Transferrin (hTF) cDNA. A human liver cDNA library constructed in the *E. coli* expression vector pKT-218 (Prochownik, E. V. et al (1983) *J. Biol. Chem.* 258:8389-8394) provided by Dr. Stuart Orkin, (Harvard University) was screened using a synthetic oligonucleotide coding for the amino-terminal eight amino acids of serum hTF as a hybridization probe. The oligonucleotide corresponded to nucleotides 88 to 111 of the hTF cDNA sequence reported by Yang, F. et al. (1984) *Proc. Natl. Acad. Sci. USA* 81:2752-2756). The oligonucleotide was end-labeled with T4 polynucleotide kinase and $^{32}$P-ATP (Chaconas, G. and van de Sande, J. H. (1980) *Methods Enzymol.* 65:75-85), and used to screen approximately $10^5$ colonies. Restriction endonuclease mapping of positive clones and DNA sequence analysis were performed by using standard procedures with pUC19 and M13mp19 vectors, respectively (Maniatis, T. et al. (1982) *Molecular Cloning, a Laboratory Manual*, Cold Spring Harbor Laboratory, Cold Spring Harbor, N.Y.; Messing, J. (1983) *Methods Enzymol.* 101:20-78; Sanger, F. et al. (1977) *Proc. Natl. Acad. Sci. USA* 74:5463-5467).

Expression Vector and Cell Culture. The eukaryotic expression vector pNUT (Palmiter, R. D. et al. (1987) *Cell* (Cambridge, Mass.) 50:435-443) and baby hamster kidney (BHK) cells were provided by Dr. Richard D. Palmiter (Howard Hughes Medical Institute, University of Washington). After synthesis, oligonucleotides were purified on $C_{18}$ reverse-phase columns (Sep-Pak, Waters Associates; Atkinson, T. and Smith, M. (1984) *Oligonucleotide Synthesis: A Practical Approach* (Gait, M. J., Ed.) pp 35-81, IRL Press, Oxford). Site-directed mutagenesis was performed by using the method of Taylor, J. W. et al. (1985) *Nucleic Acids Res.* 13:8749-8764). Plasmid DNA was prepared from *E. coli* JM105 and purified by two successive centrifugation steps with cesium chloride density gradients.

BHK cells were grown in Dulbecco's modified essential medium (DMEM) with 10% fetal bovine serum to approximately $10^7$ cells per 10-cm dish and were subsequently transfected with 10 μg of plasmid by the calcium phosphate co-precipitation technique described by Searle, P. F. et al. (1985) *Mol. Cell. Biol.* 5:1480-1489). After 24 hours, the medium was changed to DMEM containing 100 μM methotrexate (MTX) and surviving cells were serially selected to 500 μM MTX. In some experiments, cells were selected immediately with 500 μM MTX. Large scale roller bottle cultures were initiated by seeding approximately $5 \times 10^7$ cells into each 850 $cm^2$ roller bottle containing 100 mL of DMEM-MTX. Cultures were induced at 80% confluency by the addition of $ZnSO_4$ to the medium to a final concentration of 0.08 mM. The medium was harvested 40 hours later.

Immune-Precipitation and Western Blotting. Immune-precipitation of cell culture medium and cell lysates was performed by the method of Van Oost, B. A. et al. (1986) *Biochem. Cell Biol.* 64:699-705). Precipitates were analyzed by electrophoresis on 12% polyacrylamide gels in the presence of $NaDodSO_4$ (Laemmli, U. K. (1970) *Nature* (London) 227: 680-685), followed by blotting onto a nitrocellulose membrane. The blot was incubated in PBS containing 0.1 mg/ml gelatin, then treated with goat anti-hTF antiserum (250-fold dilution in PBS), and finally developed with an alkaline phosphatase-conjugated, rabbit anti-goat IgG antibody according to the supplier's instructions.

Amino Acid Substitution. To incorporate 3-fluorotyrosine into the recombinant hTF/2N as a $^{19}F$ NMR probe, the culture medium was supplemented with D,L-m-fluorotyrosine (Sigma Chemical Company) at 16% of the concentration of L-tyrosine in the medium. The cells grew as well on this medium as on the medium lacking D,L-m-fluorotyrosine.

Isolation of Recombinant hTF/2N. Harvested culture medium was made 0.01% in phenylmethylsulfonyl fluoride to inhibit proteases and sufficient $Fe(III)(NTA)_2$ was added to saturate all transferrin in the medium. After stirring at room temperature, the solution was dialyzed for 24 hours versus cold running tap water, and then for a few hours versus Milli-Q purified water. Concentrated Tris-HCl buffer, pH 8.4 was added to a final concentration of 5 mM, the preparation was centrifuged to remove any debris, and was loaded onto a column (2.5×80 cm) of DEAE-Sephacel (Pharmacia) equilibrated with 10 mM Tris-HCl buffer, pH 8.4.

The column was then eluted with a linear gradient of NaCl (0 to 0.3 M) in the same buffer. Fractions showing a pink color were analyzed by $NaDodSO_4$-PAGE, and fractions containing the recombinant protein (Mr 37,000) were pooled. Such fractions also contained bovine transferrin and albumin resulting from the fetal calf serum in the tissue culture medium. After concentration of the pooled fractions to 5 mL on an Amicon PM-10 membrane, the protein was chromatographed on a column (2.5×90 cm) of Sephadex G-75 Superfine (Pharmacia-PL Biochemicals) equilibrated with 100 mM ammonium bicarbonate.

Sometimes, a second chromatographic step through this column was necessary to resolve completely the hTF/2N from the bovine proteins. At this stage, the $A_{465}/A_{410}$ was usually <1.0, indicating the presence of a contaminating heme-protein (possibly hemopexin). The hTF/2N was finally purified to homogeneity by FPLC on a column (1×10 cm) of Polyanion SI (Pharmacia) using a linear gradient of NaCl (0 to 0.3 M) in 50 mM Tris-HCl, pH 8.0 over a period of an hour at a flow rate of 1 ml/min. Fractions of 1 mL were collected. Two to four protein bands emerged from the column, depending on the iron-binding status of the protein.

$NaDodSO_4$-PAGE was performed with 5% to 12% gradient gels and urea-PAGE was performed according to a modification (Brown-Mason, A. and Woodworth, R. C. (1984) *J. Biol. Chem.* 259:1866-1873) of the Makey, D. G. and Seal, U. S. (1976) *Biochim. Biophys. Acta* 453:250-256 procedure. Electrofocusing was performed on a 0% to 50% sucrose gradient in a 110 mL glass column (LKB) with 0.8% Pharmalyte, pH 5 to 8 (Pharmacia). The column was prefocused overnight to a final current of 2 mA at 1000 V.

The protein sample in 0.2 mL was diluted with 5 mL of solution withdrawn from the middle of the gradient. The sample was then reinjected into the isodense region of the column and focusing was continued for 24 hours. The gradient was collected from the bottom of the column in 1.5 mL fractions. Individual fractions were analyzed for $A_{280}$ and for pH. Fractions with maximum $A_{280}$ were selected as representing the pIs of the apo- and iron-saturated proteins.

Iron was readily removed from the iron-protein by incubation in a buffer containing 1 mM NTA, 1 mM EDTA, 0.5 M sodium acetate, pH 4.9. The apo-protein was concentrated to a minimum volume on a Centricon 10 (Amicon), then diluted and reconcentrated twice with water and twice with 0.1 N KCl. The apo-protein had a tendency to precipitate in pure water, but redissolved readily in 0.1 M KCl. The apo-protein was made 10 mM in $NaHCO_3$ and titrated with a suitable concentration of $Fe(NTA)_2$ while monitoring the absorbance at 465 nm.

Quantitative Immunoassay of Recombinant hTF/2N. A competitive solid state immunoassay was used to assess the concentration of recombinant hTF/2N in the culture fluid and at various stages of the purification (Foster, W. B. et al. (1982) *Thromb. Res.* 28:649-661). Proteolytically-derived Fe-hTF/2N (Lineback-Zins, J. and Brew, K. (1980) *J. Biol. Chem.* 255:708-713) was radioiodinated (Fraker, P. J. and Speck, J. C., Jr. (1978) *Biochem. Biophys. Res. Commun.* 80:849-857) with Iodogen (Pierce Chemical Company) and used as the standard. The monoclonal anti-hTF antibody HTF-14 was used as the probe (Bartek, J. et al. (1984) *Folia Biol.* (Prague) 30:137-140). This antibody recognizes only the amino-terminal lobe of hTF (Mason, A. B. et al. (1988) *Br. J. Haematol.* 68:392-393) and does not recognize bovine transferrin (Penhallow, R. C. et al. (1986) *J. Cell. Physiol.* 128:251-260).

Amino-Terminal Sequence Analysis. The amino-terminal sequences of both the minor and major-forms of recombinant hTF/2N were determined on an Applied Biosystems 470A Protein Sequencer in the Given Analytical Facility at the University of Vermont.

Periodic Acid-Schiff Stain. The presence of oligosaccharides in the recombinant hTF/2N was determined by staining the protein with periodic acid-Schiff reagent (Fairbanks, G. et al. (1971) *Biochemistry* 10:2606-2617).

Nuclear Magnetic Resonance Spectroscopy. Proton and fluorine NMR spectra were obtained on the 5.872 Tesla Bruker WM NMR spectrometer in the Camille and Henry Dreyfus NMR Laboratory, Department of Chemistry, University of Vermont, operating in the Fourier transform mode with quadrature detection. An $^{19}$F probe was provided by Dr. Christopher W. Allen of that department. For proton spectra, spectrometer settings were as described previously (Valcour, A. A. and Woodworth, R. C. (1987) *Biochemistry* 26:3120-3125). For $^{19}$F spectra, the sweep width was 30,000 Hz, the acquisition time was 0.279 seconds, a receiver delay of 2.0 seconds intervened between acquisition and pulse of 15.0 μs (90°) and the sample was at 303° K. $^{19}$F chemical shifts are relative to 0.1M trifluoroacetic acid in $^2H_2O$. Protein samples were 6 to 8 mg in 0.1 mL of 99.8 atom % $^2H_2O$, and spectra were run on these samples in 0.1 mL capsules inserted into standard 5 nm NMR tubes containing $^2H_2O$. Free induction decays of $^{19}$F spectra were subjected to a line-broadening of 10 Hz prior to Fourier transformation.

Results

Isolation of Human TF cDNA. Approximately 100,000 colonies of a human liver cDNA library (Prochownik, E. V. et al. (1983) *J. Biol. Chem.* 258:8389-8394) were screened by using a 24 base oligonucleotide to the 5' sequence of the human TF cDNA as a hybridization probe. A single positive colony was obtained. Extensive restriction enzyme mapping of the plasmid isolated from this clone agreed completely with the patterns predicted from the human TF cDNA isolated from the same library by Yang, F. et al. (1984) *Proc. Natl. Acad. Sci. USA* 81:2752-2756. DNA sequence analysis of the 5'- and 3'-termini of this clone confirmed that it was identical to the full-length clone isolated by Yang et al. All subsequent sequence analysis performed during the mutagenesis and subcloning of this cDNA conformed exactly to the sequence reported previously.

Vector Construction and Expression. Two translational stop codons and a unique HindIII recognition site were introduced into the linker region between the amino- and carboxy-terminal domains of the hTF cDNA sequence by oligonucleotide-directed mutagenesis. The predicted translation sequence from this construct ends at Asp-337, according to the serum hTF numbering sequence (MacGillivray, R. T. A. et al. (1983) *J. Biol. Chem.* 258:3543-3553).

The expression vector pNUT (Palmiter, R. D. et al. (1987) *Cell* (Cambridge, Mass.) 50:435-443) contains a mouse metallothionein-1/human growth hormone gene fusion that has been shown to direct high levels of human growth hormone in transgenic mice (Palmiter, R. D. et al. (1983) *Science* (Washington, D.C.) 222:809-814). Important functional features of this vector include a mouse metallothionein-1 promoter to induce cDNA transcription in the presence of heavy metals, pUC18 sequences to allow replication and selection in *E. coli*, and a dihydrofolate reductase (DHFR) cDNA driven by the SV40 early promoter to allow selection in cell culture. The DHFR cDNA encodes a mutant form of the enzyme which has a 270-fold lower affinity for the competitive inhibitor methotrexate (MTX) (Simonsen, C. C. and Levinson, A. D. (1983) *Proc. Natl. Acad. Sci. USA* 80:2495-2499). This allows for the immediate selection of transfected cells in very high concentrations (0.5 mM) of MTX and abrogates the need for a recipient cell line that is deficient in DHFR.

To construct the expression vector pNUT-hTF/2N, the BamHI-HindIII fragment from the bacterial expression vector was isolated (FIG. 1). An HpaII-BamHI fragment from the original transferrin cDNA clone was also isolated (FIG. 1). These two fragments were then ligated into M13mp18 replicative form DNA that had been cut with AccI and HindIII. Replicative form DNA from the resulting M13 phage was isolated, the insert released by cleavage with XbaI and HindIII, and the ends made blunt ended. These steps ensured that the fragment included the translational stop signals, retained the natural signal sequence for the protein, and was free of the dG/dC tail found in the original vector (FIG. 1). This fragment was inserted into SmaI-cut pNUT, thus replacing the human growth hormone gene with a hTF/2N encoding cDNA, but leaving the transcriptional termination signal from the growth hormone gene intact. This plasmid was transfected into BHK cells and the resulting transformants were selected in the presence of MTX.

To analyze the mRNA transcripts produced by the transfected BHK cells, total RNA was electrophoresed on an agarose gel in the presence of formaldehyde (Maniatis, T. et al. (1982) *Molecular Cloning, a Laboratory Manual*, Cold Spring Harbor Laboratory, Cold Spring Harbor, N.Y.). After transfer to nitrocellulose, the blot was analyzed by using an oligonucleotide to the 3' untranslated region of the hGH gene as a hybridization probe. An inducible mRNA of approximately 1.4 kb was detected in the transfected cell line but not in mock-infected BHK cells (data not shown). This agreed with the predicted size of the hTF/2N mRNA, including the expected hGH 3' untranslated sequence and poly (A) tail.

Figure 2:
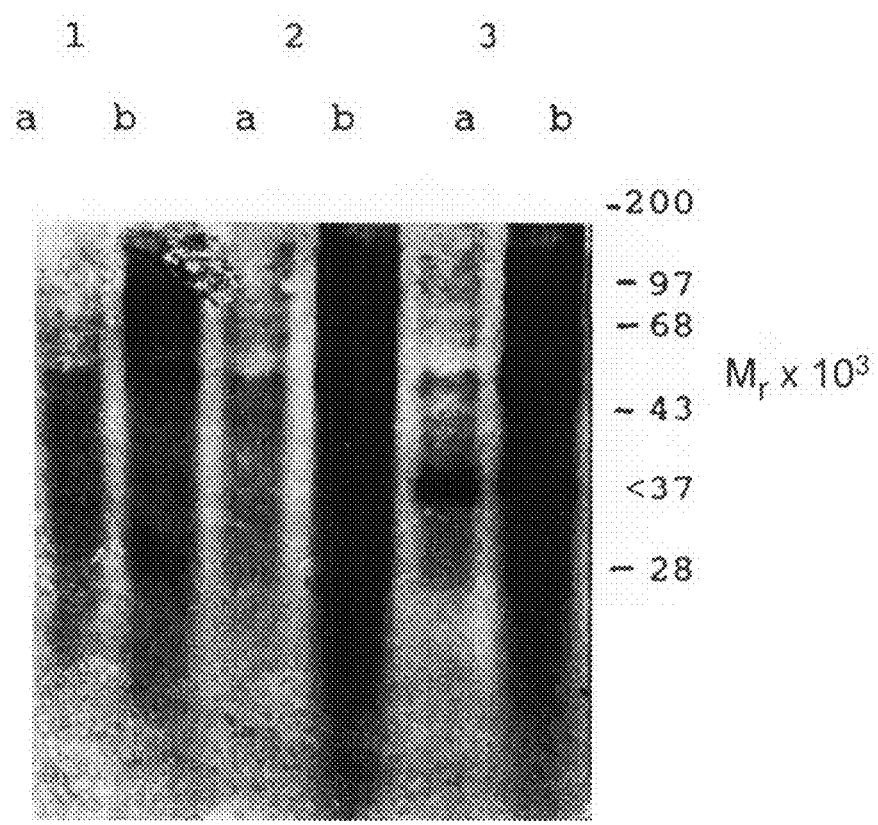
FIG. 2 shows a Western blot of immuno-precipitates from various baby hamster kidney cell lines. Samples of cell lysates (a) and medium (b) from Zn-induced cell cultures were precipitated with anti-hTF antiserum. Samples of the resuspended pellets were analyzed by $NaDodSO_4$—PAGE, transferred to nitrocellulose and developed with anti-hTF antiserum followed by alkaline phosphatase conjugated anti-IgG. The hGH-pNUT and hTF/2N-pNUT transformed cell lines were selected in 500 μM MTX and all cell culture was performed in DMEM/10% fetal calf serum. Lane 1, BHK cells; lane 2, hGH-pNUT transfected BHK cells; lane 3, hTF/N2-pNUT transfected BHK cells. The positions of molecular weight markers ($\times 10^3$) are indicated to the right of the blot, the position of the additional protein band of $M_r$ 37,000 is also indicated (<37) to the right of the blot.

To analyze the polypeptides produced by the transformed BHK cells, Western blot analysis was performed both on cell lysates and the medium of various cell lines (FIG. 2). Samples of BHK cells, BHK cells containing the hGH-pNUT plasmid, and BHK cells containing the hTF/2N-pNUT plasmid were grown in DMEM (BHK cells) or DMEM-MTX (BHK cells containing pNUT vectors). When the cells were reaching confluence, samples of medium were taken and cell lysates were prepared. These samples were incubated successively with goat anti-hTF antiserum and formalin-fixed *S. aureus* cells (Van Oost, B. A. et al. (1986) *Biochem. Cell Biol.* 64:699-705).

Bound proteins were eluted by incubation with $NaDodSO_4$, electrophoresed on a polyacrylamide gel, and transferred to a nitrocellulose membrane. The membrane was then incubated with goat anti-hTF antiserum and rabbit anti-goat immunoglobulin conjugated to alkaline phosphatase. When cell lysates or medium from BHK cells (FIG. 2, lanes 1a and 1b) or BHK cells with hGH-pNUT plasmid (FIG. 2, lanes 2a and 2b) were analyzed, only the expected goat immunoglobulin bands (Mr 25,000 and 50,000) from the original goat anti-hTF antibodies and a small amount of cross-reacting material were observed. However, an additional band of Mr 37,000 was observed in cell lysates (FIG. 2, lane 3a) or medium (FIG. 2, lane 3b) of the BHK cells containing the hTF/2N-pNUT plasmid. The molecular weight of this polypeptide chain is in excellent agreement with the molecular weight of the hTF/2N molecule (37,833) calculated from the amino acid sequence.

The homogeneity of the hTF/2N product indicates the successful removal of signal sequence as cell lysate and secreted samples comigrate on SDS-PAGE. The anti-serum appears to be highly specific for human TF species, since little bovine TF is apparent in the precipitates.

In large scale cultures of the hTF/2N cell line grown in roller-bottles, the concentration of hTF/2N in the medium was approximately 10-15 μg/ml as detected by radioimmunoassay.

Isolation and Characterization of Recombinant hTF/2N. Recombinant hTF/2N was purified by a three-step procedure that led routinely to an 80% yield of the major form of the protein, based on radioimmunoassay. The final purification on Polyanion SI led to quantitative resolution of the apo- and iron-saturated forms of both the minor (<5%) and major constituents of the protein (FIG. 3, panel A), as corroborated by urea-PAGE (FIG. 3, panel C). Note that on urea-PAGE the slowest moving bands are apo-hTF/2N and the faster moving bands are Fe-hTF/2N. SDS-PAGE gels (FIG. 3, panel B) showed the major and minor forms of recombinant hTF/2N to be monodisperse, of equal molecular weight and the major component to be free of carbohydrate by PAS stain (data not shown).

Figure 4:
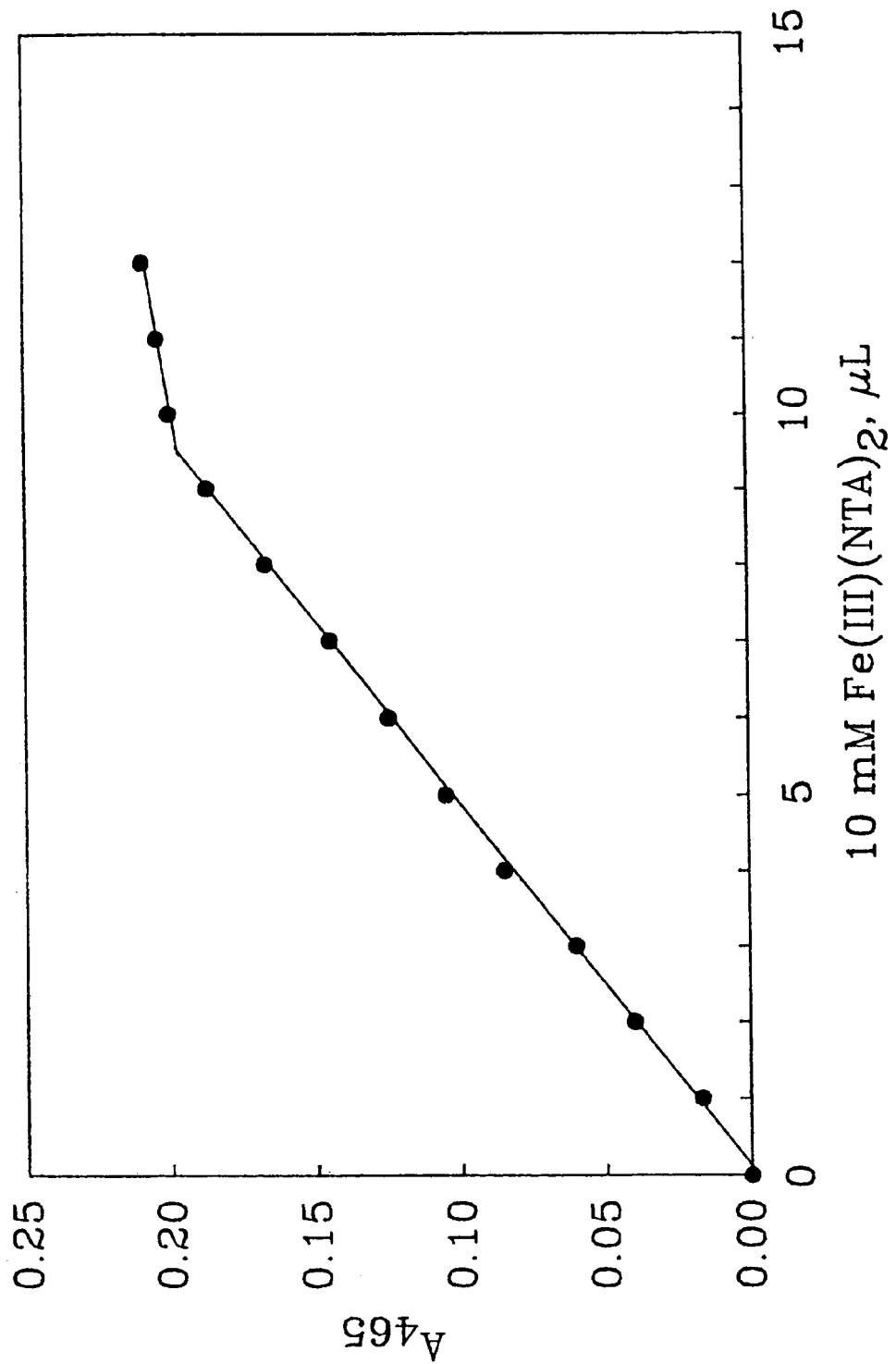
FIG. 4 shows titration of the major form recombinant hTF/2N with 10 mM $Fe(III)(NTA)_2$. The amount of protein was 3.68 $A_{280}$ units in 1.00 mL of 10 mM $NaHCO_3$. Visible spectra were run 5-10 minutes after each addition of iron to the magnetically stirred cuvette.

In general these preparations appear to have better monodispersity than proteolytically derived hTF/2N (Lineback-Zins, J. and Brew, K. (1980) *J. Biol. Chem.* 255:708-713) (FIG. 3). For example, the chromatographic peaks are more regular for the former, and the number of bands on urea-PAGE is greater for the latter. Spectral ratios for the iron-saturated recombinant protein are typically $A_{280}/A_{465}=21$ and $A_{465}/A_{410}=1.38$, which compare favorably with values for pure diferric transferrin isolated from human plasma. Titration of 3.68 $A_{280}$ units of the apo-protein with $Fe(NTA)_2$ yields a slope corresponding to an $E_{465}(mM)=2.1$ and gives for the apo-protein $E_{280}(mM)=38.8$ (FIG. 4), both reasonable values for a half-transferrin molecule (Lineback-Zins, J. and Brew, K. (1980) *J. Biol. Chem.* 255:708-713; Zak, O. et al. (1983) *Biochim. Biophys. Acta* 742:490-495). The pI's for the apo- and Fe-hTF/2N were 6.5 and 5.4, respectively.

Amino-terminal sequence analysis of both the minor and major forms of recombinant hTF/2N gave results identical to those found (MacGillivray, R. T. A. et al. (1983) *J. Biol. Chem.* 258:3543-3553) for holo-hTF from serum (Table 1).

Figure 5A:
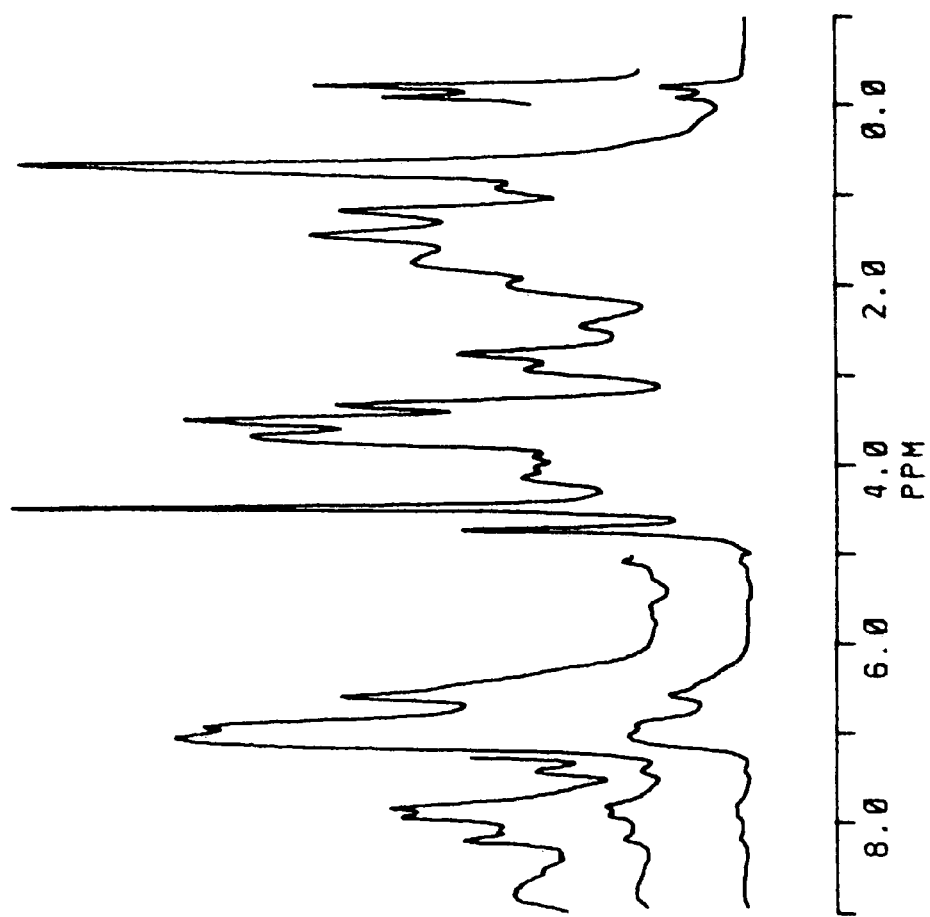
FIGS. 5A and 5B shows proton magnetic resonance spectra of recombinant hTF/2N. (5A) Fourier transform spectrum with a line broadening of 2 Hz. (5B) Convolution difference spectrum with a line broadening of 4 Hz and DC=4.0, NS=68, 500. The protein sample was 8 mg in 0.1 mL of 0.1 M KCl in $^2H_2O$.
Figure 5B:
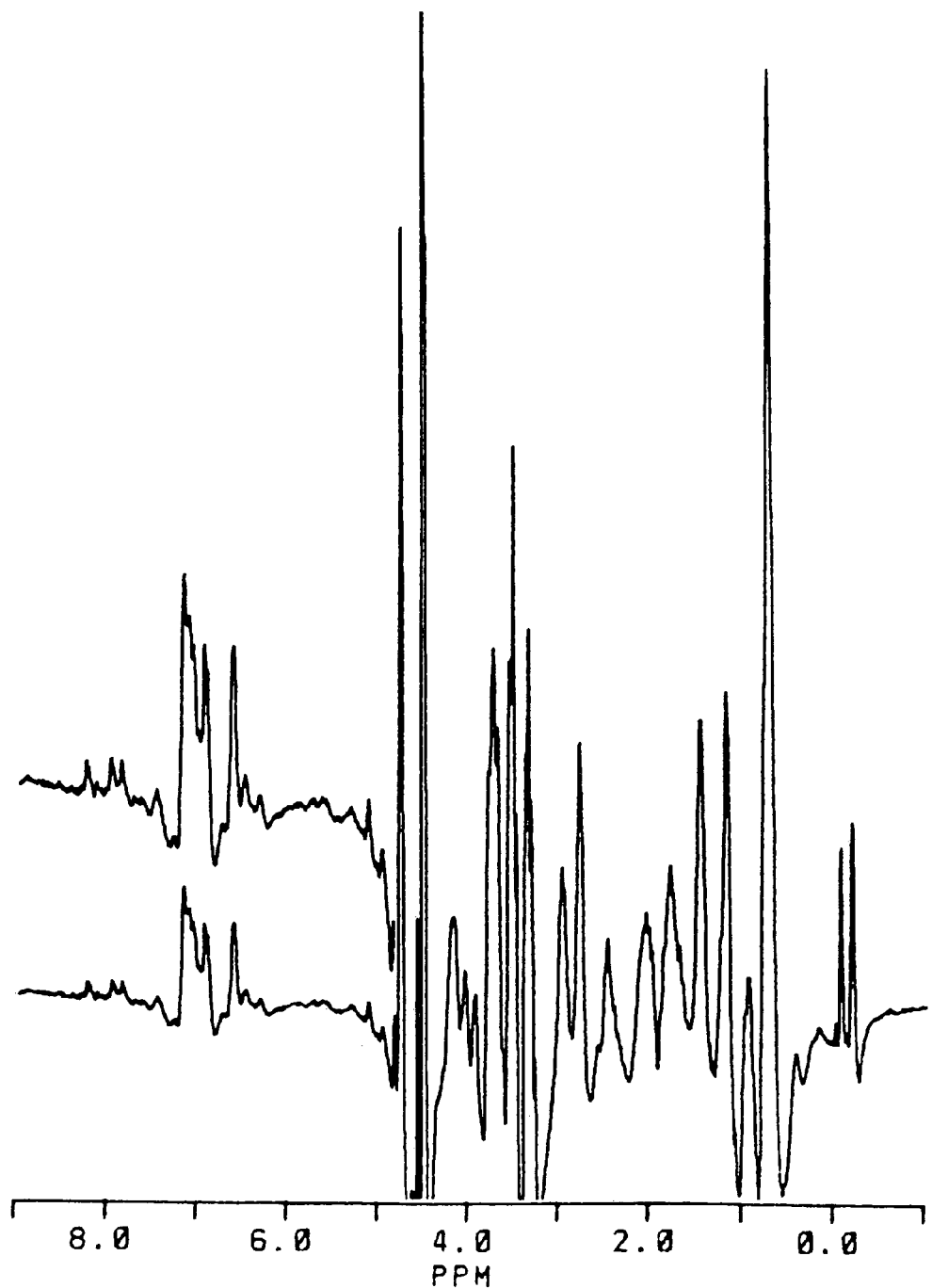
Figure 6:
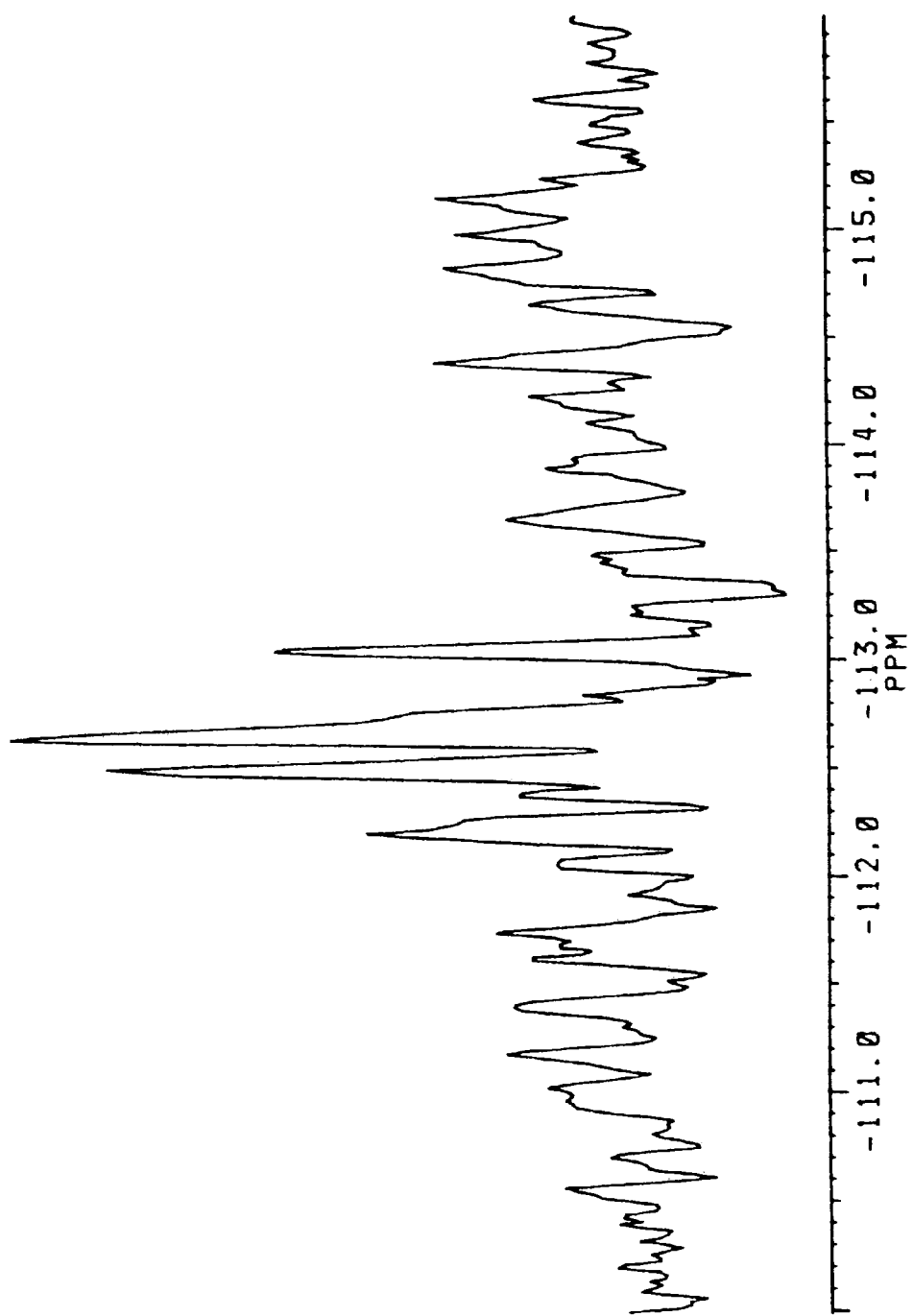
FIG. 6 shows the $^{19}F$ nuclear magnetic resonance spectrum of m-F-Tyr recombinant hTF/2N. The figure shows a Fourier transformation with a line broadening of 10 Hz, NS=30,000. The protein sample was 6 mg in 0.1 mL of 0.1 M KCl in $^2H_2O$; the reference was 0.1 M trifluoroacetic acid in $^2H_2O$.
Figure 7:
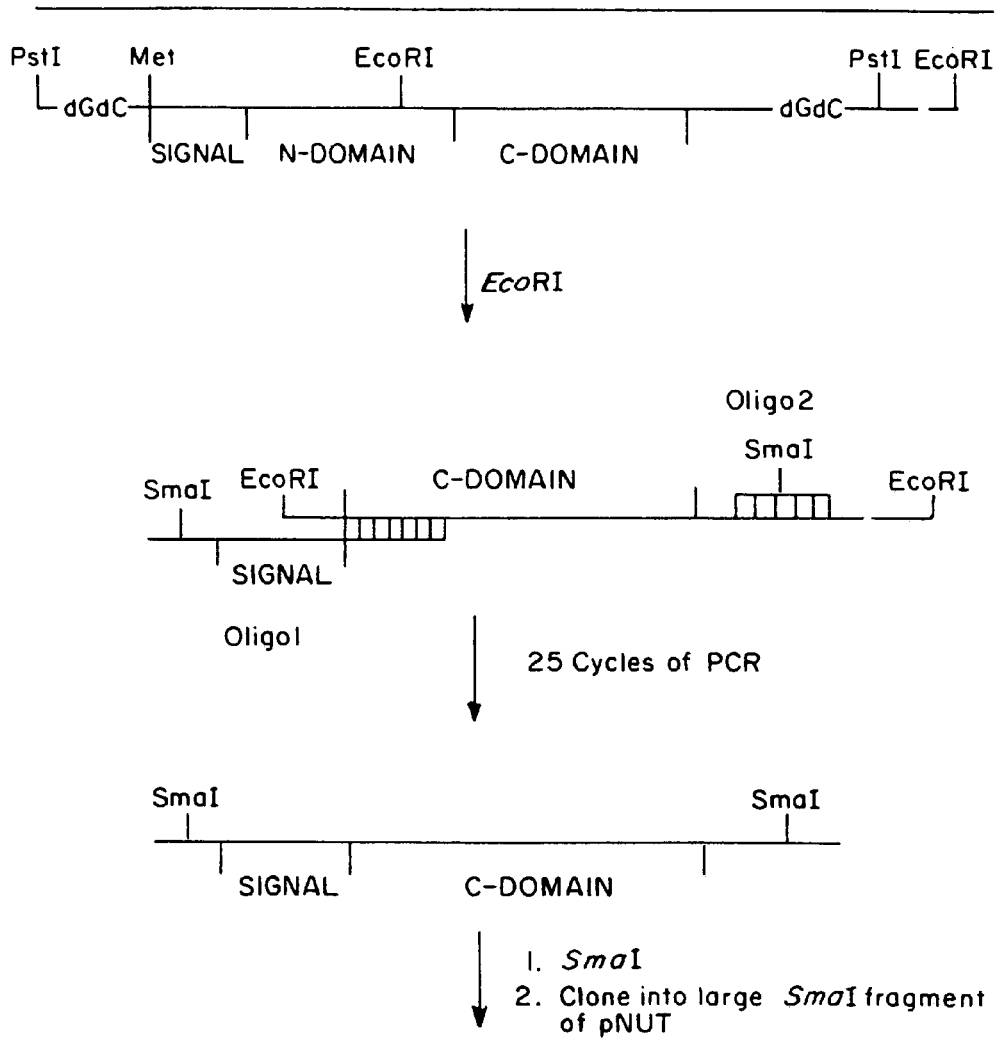
FIG. 7 shows two separate oligonucleotides used as PCR primers to create the hTF/2C coding sequence. An EcoRI restriction fragment including coding sequence for the entire carboxy lobe was used as a template for 25 rounds of PCR amplification. Oligonucleotide 1 includes a SmaI recognition site and the natural hTF signal sequence at its 5' end and matches the coding sequence for amino acids 334-341 of hTF at its 3' end. Oligonucleotide 2 matches sequence in the 3' untranslated region of the hTF cDNA and introduces a second SmaI recognition sequence at this site.

The proton NMR spectrum of the recombinant protein (FIG. 5) is very similar to that for the proteolytically-derived hTF/2N (Valcour, A. A. and Woodworth, R. C. (1987) *Biochemistry* 26:3120-3125), but the resonance lines are sharper for the recombinant protein. The $^{19}F$ NMR spectrum of the protein derived from a cell culture grown on medium supplemented with m-F-tyrosine (FIG. 6) shows four well-resolved resonances, two possibly having an unresolved shoulder.

The pNUT based hTF/2N construction described here produces high levels of recombinant protein without the need for a DHFR-deficient cell line or tedious resistance amplification procedures. BHK cells are well-suited for economical, large scale growth and we are currently examining their growth characteristics on micro-carrier supports in bioreactor vessels. By using either roller bottles or a fermentor with a capacity of several liters, we can easily produce sufficient recombinant protein even for techniques such as NMR that traditionally have required a high concentration of protein.

The minor form of recombinant hTF/2N isolated on Polyanion SI migrates more slowly than the major form on urea-PAGE (FIG. 3, panel C), but at the same rate on SDS-PAGE (FIG. 3, panel B). Thus, the apparent molecular weights are the same but the relative degrees of unfolding in 6 M urea differ. Note that the proteolytically-derived apo-hTF/2N shows even faster migrating species in 6 M urea (FIG. 3, panel C, fractions g and h).

Contamination of apo-hTF/2N with Fe-hTF/2N and vice versa on these gels arises from the method of pooling FPLC fractions, from some loss of bound iron on the urea gel and from binding of contaminating iron during workup of the FPLC samples. Identical N-terminal sequences (Table 1) show that the signal peptide has been removed from both minor and major forms of the recombinant protein. As in hTF/2N from human serum (Lineback-Zins, J. and Brew, K. (1980) *J. Biol. Chem.* 255:708-713), the recombinant hTF/2N is non-glycosylated. The cause of the difference between major and minor forms of hTF/2N is unknown at present. The minor form has never represented more than 5% of the total recombinant protein and is usually less than 1%. Thus, the goal of isolating a monodisperse recombinant hTF/2N (the major form) has been achieved.

The iron binding behavior, pIs, migration on $NaDodSO_4$-PAGE and urea-PAGE and proton NMR spectra of the recombinant hTF/2N match reasonably well those of the hTF/2N derived from amino terminal monoferric hTF by proteolysis with thermolysin (Lineback-Zins, J. and Brew, K. (1980) *J. Biol. Chem.* 255:708-713; Valcour, A. A. and Woodworth, R. C. (1987) *Biochemistry* 26:3120-3125), except as noted above. The major form of the recombinant protein shows a higher degree of monodispersity (FIG. 3) and its proton NMR

TABLE 1

Amino-Terminal Sequence of Human Transferrin and of the Recombinant Human Transferrin Amino-Terminal Half-Molecule[a]

| Protein | Amino Acid Sequence | Reference |
|---|---|---|
| human serum transferrin | V-P-D-K-T-V-R-W-C-A-V-S- | MacGillirvray et al. (1983) (SEQ ID NO: 5) |
| recombinant hTF/2N (major)[b, c] | V-P-D-K-T-V-R-W-X-A-V-S- | this report (SEQ ID NO: 6) |
| recombinant hTF/2N (minor)[d] | V-P-D-K-T-V- | this report (SEQ ID NO: 7) |

[a]The recombinant hTF/2N sequences were determined on an Applied Biosystems 470A protein sequencer. Approximately 200 pmol of each sample was analyzed.
[b]Twelve sequencer cycles were analyzed.
[c]No residue was identified at cycle 9; however, cysteine residues were not modified prior to the analysis.
[d]Six sequencer cycles were analyzed.

By using recombinant DNA technology, a hTF/2N molecule is produced that functions identically with the proteolytically derived species as judged by several independent criteria. This represents the first reported expression in a stable cell culture system of a functionally active form of this important iron transport protein.

spectrum shows sharper resonance lines than does the proteolytically derived hTF/2N. There has been insufficient minor form for analysis by NMR.

Previous studies of the incorporation of m-fluorotyrosine into alkaline phosphatase from *E. coli* have established the efficacy of $^{19}F$ NMR for specifically probing the tyrosyl residues in a protein (Sykes, B. D. et al. (1974) *Proc. Natl. Acad.*

Sci. USA 71:469-473; Hull, W. E. and Sykes, B. D. (1974) Biochemistry 13:3431-3437). Incorporation of m-F-tyrosine into the recombinant hTF/2N proves that selective amino acid substitution is possible in this cell culture system and gives access to a specific NMR probe of tyrosyl side chains. This preparation behaves in all respects like the non-modified protein as described above for the non-substituted recombinant. When the cell culture conditions have been optimized to achieve higher levels of incorporation, changes in the $^{19}F$ NMR spectrum on addition of paramagnetic and diamagnetic metals and on changes in pH can be useful in studying the tyrosyl residues specifically involved in metal binding. Incorporation of selectively deuterated aromatic amino acids can allow dissection of the aromatic region of the proton NMR spectrum of the protein in similar fashion to the studies on lysozyme from Japanese quail (Brown-Mason, A. et al. (1981) *J. Biol. Chem.* 256:1506-1509).

II. Production of Recombinant Transferrin Half-Molecule Comprising Carboxy Terminal Lobe.

An EcoRI restriction fragment including the coding sequence for the carboxy lobe of hTF was isolated from the full length hTF cDNA and then used as a template for PCR-directed mutagenesis (FIG. 2). Two oligonucleotides were synthesized to be used as PCR primers. Oligo 1 encodes a SmaI recognition site, followed by sequence encoding the natural signal sequence of hTF, followed by sequence matching the coding sequence for amino acids 334-341. The second oligonucleotide matches the complement of the 3' nontranslated region of the hTF cDNA and introduces a SmaI recognition sequence 3' to the normal translation termination site (nucleotides 2125-2127 using the numbering system of Yang, F. et al. (1984) *Proc. Natl. Acad. Sci. USA* 81:2752-2756). Twenty-five rounds of PCR amplification using Taq polymerase (Perkin Elmer) resulted in the desired DNA fragment which splices the natural signal sequence of hTF to the C lobe coding sequence. This fragment was then digested with SmaI and ligated with the large SmaI fragment of pNUT as for the hTF/2N expression studies.

III. Production of Recombinant Full Length Transferrin.

The coding sequence for human serum transferrin was assembled from restriction enzyme digestion fragments derived from the full-length cDNA clone isolated from a human liver library described above. Since the parental plasmid (pKT-218) of the original clone had a limited number of unique restriction enzyme recognition sites, a series of cloning steps was required to introduce the coding sequence into a convenient vector. This process was initiated by cloning a HpaII/BamHI fragment from the 5' end of the cDNA into the vector pUC18 (Messing, J. (1983) *Meth. Enzymol.* 101:20-28). The resulting plasmid was digested with BamHI and HindIII and a BamHI/HindIII fragment from the human transferrin cDNA was cloned adjacent to the initial fragment. The resulting plasmid was then digested with HindIII and PstI and a final HindIII/PstI fragment from the 3' end of the transferrin cDNA was cloned to complete the assembly of the full-length coding sequence. Digestion of the resulting plasmid with SacI and SphI released the full-length coding sequence as a single restriction fragment which was subsequently made blunt using T4 DNA polymerase and dNTPs and then cloned into the large SmaI fragment of pNUT (Palmiter et al. (1987) *Cell* 50:435-443) as described for the N- and C-terminal transferrin half-molecule coding sequences.

Plasmid DNA was prepared from *E. coli* JM105 and purified by two successive centrifugation steps with cesium chloride gradients. Baby hamster kidney (BHK) cells were grown in Dulbecco's Modified Eagles' medium-Ham's F-12 nutrient mixture (DMEM-F-12) (Gibco; Sigma) with 10% fetal bovine serum to approximately $10^7$ cells per 100 mm dish and were subsequently transfected with 10 µg of plasmid by the calcium phosphate coprecipitation technique described by Searle et al. (1985) *Mol. Cell. Biol.* 5:1480-1489. After 24 hours, the medium was changed to DMEM-F-12 containing 500 µM methotrexate to select the plasmid containing cells. Once selected, the cells were serially passaged at approximately 80% confluency with phosphate buffered saline containing EDTA (0.2 gm/l) to five 100-mm dishes, then to five T-175 flasks and finally to five expanded surface roller bottles (200 ml each). At the T-175 passage, a serum substitute, ULTROSER-G™ (Gibco) (serum substitute), at a level of 1% was used in place of fetal calf serum in DMEM-F-12 lacking phenol red.

It was found that once production levels were high (approximately 100 µg/ml of medium), medium without ULTROSER G™ (Gibco) (serum substitute) could sustain production of recombinant protein for at least two passages. This greatly simplified the isolation of the expressed full-length recombinant human serum transferrin. To isolate the recombinant protein, harvested culture medium is made 0.01% with respect to phenylmethanesulfonyl fluoride and sodium azide to inhibit proteases and bacterial growth respectively. Sufficient $Fe^{3+}$ (nitrilotriacetic acid)$_2$ is added to saturate the transferrin present. The medium is reduced in volume to <10 ml and the transferrin is purified by passage over an anion exchange column (Polyanion SI, 1×10 cm) as described for the recombinant amino terminal human transferrin half-molecule above.

The isolated recombinant full-length human serum transferrin displays some heterogeneity on this column attributed to variation in the glycosylation pattern. The protein is monodisperse on NaDod $SO_4$-polyacrylamide gel electrophoresis and has a spectrum and spectral ratios which are comparable to purified human serum transferrin.

IV. Production of Mutant Transferrins.

Substitution mutants are designated using the conventional single letter amino acid symbol of the wild type (native) residue, followed by the positional number of the replacement in the primary sequence, (where valine of the mature protein is designated position 1) followed by the symbol for the replacement residue. For example, a mutant in which aspartic acid residue at position 63 is replaced by a serine residue would be designated D63S.

The production of hTF/2N mutants was accomplished by two techniques. A D63S substitution was prepared using the method of Nelson, R. M. and Long, G. L. (1989) *Analyt. Biochem.* 180:147-151. Briefly, a HpaII/BamHI fragment from the 5' end of the hTF/2N coding sequence was subcloned into pUC18 and then used as a template for a two step PCR-based mutagenesis procedure. The resulting DNA fragment was then recloned into M13mp18 and the sequence of the mutant construction was confirmed by dideoxy sequence analysis. The fragment was then released from the double stranded form of the sequencing vector by digestion with XbaI and BamHI and then ligated to a BamHI/HindIII fragment from the original hTF/2N construction to produce a full length D63S-hTF/2N coding sequence, the fidelity of this splicing was confirmed by restriction digestion analysis and was subsequently cloned into pNUT as before.

The substitution mutants G65R, D63C, K206Q and H207E were produced by subcloning the entire hTF/2N coding sequence into M13mp18, which was then used as a template for oligonucleotide-directed mutagenesis (Zoller, M. J. and Smith, M. (1983) *Meth. Enzymol.* 100:458-500) using the dut⁻, ung⁻ selection procedure (Kunkel, T. A. (1985) *Proc. Natl. Acad. Sci. USA* 82:488-492). Following mutagenesis, the entire coding sequence for the mutant sequences was confirmed by dideoxy sequence analysis using sequencing primers targeted along the length of the coding sequence at 250 bp intervals. The desired coding sequences were then released by restriction digestion, made blunt and inserted into pNUT as before.

pNUT plasmids have been constructed containing the cDNA a) for full-length human serum transferrin (hTF) and b) for various site-directed mutants of the amino-terminal half-molecule (hTF/2N). These mutants include 1) D63S patterned on the naturally occurring mutation found in the C-terminal half of human melanoferrin, b) G65R patterned on the naturally occurring mutant found in the C-terminal half of hTF from a patient in England, c) K206Q based on the wild type mutation in the C-terminal half of ovotransferrin (oTF) from hen's egg white, d) H207E based on the wild type mutation in human lactoferrin (hLTF) and e) D63C as an attempt to change the metal selectivity of the iron binding site. All of these constructions have been expressed in stable transformants of baby hamster kidney cells in 10 to 100 mg amounts of recombinant protein. In addition pNUT plasmids have been constructed containing the full length cDNA for oTF and chimeric cDNAs for hTF/2N-oTF/2C and oTF/2N-hTF/2C.

Characteristics of the site-directed mutants include: the D63S mutant does bind iron (contrary to speculations in the literature) but much less avidly than the wild type protein. For instance, this mutant loses its bound iron on electrophoresis in PAGE gels containing 8 M urea, whereas the wild type retains its bound iron. The maximum in the visible spectrum lies at 422 nm in contrast to that or the wild type at 470 nm. The G65R mutant binds iron less tightly than does the wild type and has a visible maximum at 470 nm. The K206Q mutant binds iron much more avidly than does the wild type, as does its model, oTF/2C. Whereas the red color of the wild type iron protein disappears very rapidly in 0.5 M acetate buffer at pH 4.9, containing 1 mM each of EDTA and NTA, the mutant loses no color at all and requires pH 4 and 1 mM deferoxamine to release its bound iron. The apo-mutant appears to rebind iron more slowly than the wild type protein. The visible maximum lies at 460 nm for this mutant. The H207E mutant also binds iron more avidly than does the wild type.

The full length recombinant hTF runs at the same rate as the serum-derived protein on SDS-PAGE.

V. Removal of Glycosylation Sites from hTf.

Human serum transferrin contains two N-linked oligosaccharides, at Asn-413 and Asn-611 (MacGillivray et al. (1982) *PNAS USA* 79:2504-2508), corresponding to AAT and AAC codons in the cDNA sequence, respectively (Yang et al. (1984) *Proc. Natl. Acad. Sci. USA* 81:2752-2756). These codons were converted to GAT and GAC by oligonucleotide-directed mutagenesis using the dut$^-$ and ung$^-$ method (Kunkel, T. A. (1985) *Proc. Natl. Acad. Sci. USA* 82:488-492). The mutagenic oligonucleotides:

```
5'-GCAGAAAACTACGATAAGAGCGATAAT-3'     (SEQ ID NO: 3)

5'-CTATTTGGAAGCGACGTAACTGACTGC-3'     (SEQ ID NO: 4)
```

(the mutated codons are underlined) were synthesized on an Applied Biosystems 391 DNA synthesizer, and were purified by reverse-phase chromatography using a SEP-PAK (Waters) column (Atkinson, T. and Smith, M. (1984) *Oligonucleotide Synthesis: A Practical Approach* (Gait, M. J., Ed.) pp 35-81, IRL Press, Oxford).

Figure 8:
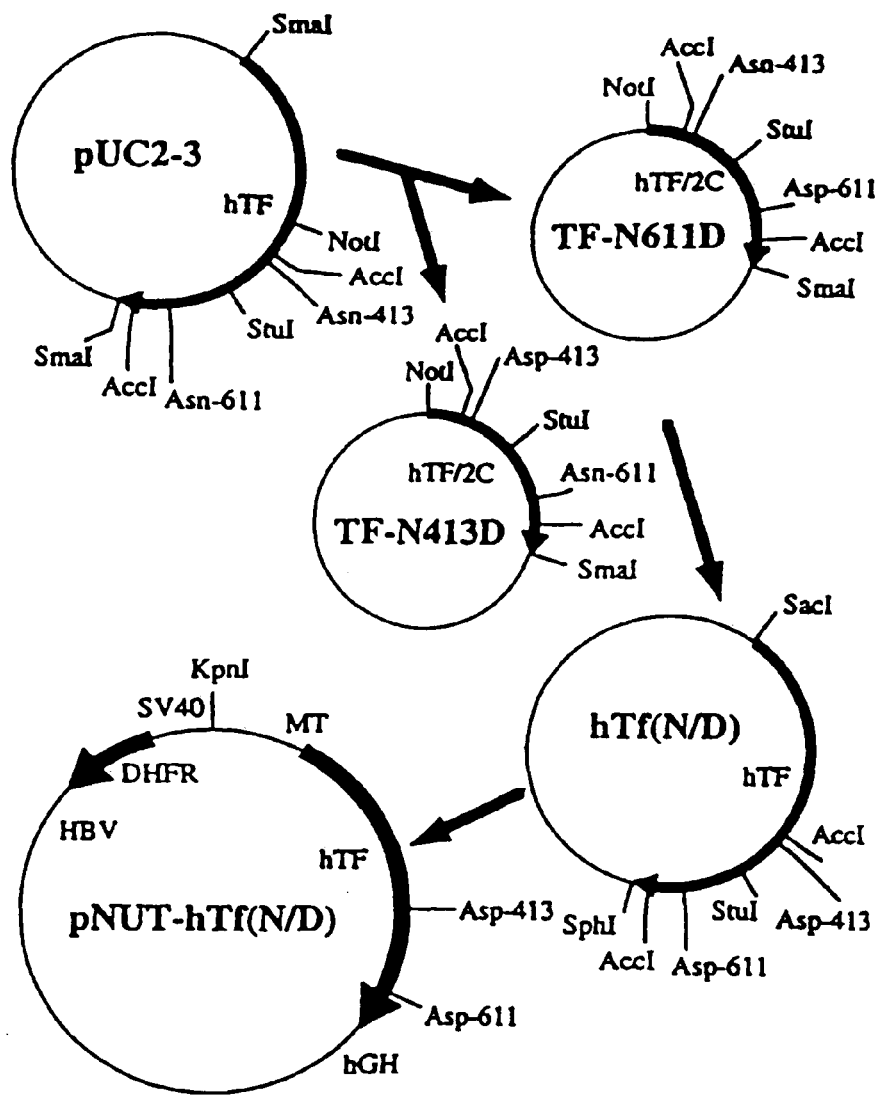
FIG. 8 shows the construction of the hTf N413D/N611D expression vector in pNUT. Using a plasmid called pUC2-3 which contains the DNA coding region for the C-terminal lobe of hTf, each of the two mutagenic oligonucleotides described in Example V was used separately to introduce the desired mutations. The two resulting plasmids, Tf-N413D and Tf-N611D, were cut with AccI and StuI; the DNA fragments containing the mutated residues were removed from agarose gel slices and ligated into the AccI site of a full-length Tf cDNA clone in pUC19 to give hTf(N/D). This plasmid was cleaved with SacI and SphI, the ends were made blunt, and the fragment was cloned into the SmaI site of pNUT to give pNUT-hTf(N/D). In this plasmid, the cDNA is under the control of the metallothionein promoter (MT) and the human growth hormone transcription termination signals (hGH). pNUT also contains the SV40 early promoter (SV40) driving expression of a mutated form of the dihydrofolate reductase (DHFR) cDNA using transcription termination signals from human hepatitis B virus (HBV).

The template for the mutagenesis was a plasmid containing the DNA coding sequence for the C-lobe of transferrin cloned into pUC named pUC2-3; as shown in FIG. 8, this plasmid contains a NotI site in the interlobe bridge coding region and a SmaI site in both the 5' and 3' untranslated regions. Each of the two mutagenic oligonucleotides was used separately to introduce the desired mutations into pUC2-3; the resulting plasmids were Tf-N413D and Tf-N611D (see FIG. 8). The presence of the mutated codons was confirmed by DNA sequence analysis (Sanger, F. et al. (1977) *Proc. Natl. Acad. Sci. USA* 74:5463-5467). Each plasmid was cut with AccI and StuI, the DNA fragments were separated by agarose gel electrophoresis, and the fragments containing the mutated residues were recovered from gel slices using GENECLEAN (Bio101, La Jolla, Calif.). The fragments were then ligated back into the AccI site of the full-length transferrin cDNA clone in pUC19. The structure of the final construction, hTf (N/D), was confirmed by restriction mapping and DNA sequence analysis. The transferrin cDNA was then released with SacI and SphI; the ends were made blunt by treatment with the Klenow fragment of DNA polymerase I in the presence of dNTPS and ligated directly into pNUT restricted with SmaI (Palmiter, R. D. et al. (1987) *Cell* 50:435-443) as described for the N- and C-terminal transferring half-molecule coding sequences. The correct orientation of the pNUT-hTf(N/D) clone was confirmed by restriction-endonuclease mapping.

The pNUT-hTf (N/D) clone was then treated in the same manner as described for the full recombinant length transferrin. The resulting transformations were selected using 500 μM MTX.

The isolated hTfN413D/N611D mutant protein was monodisperse on sodium dodecyl sulfate-polyacrylamide gel electrophoresis and had a spectrum and spectral ratios similar to that of serum-derived hTf. However, the hTf N413D/N611D mutant migrates slightly faster than serum-derived hTf.

VI. Cell-Binding Experiments.

HeLa S$_3$ cells were the generous gift of Dr. Joan Moehring (Department of Microbiology, University of Vermont College of Medicine). Cells were routinely grown in DMEM-F-12 containing 10% newborn calf serum. Prior to beginning a binding experiment, the cells were harvested with Versene, and taken up in Joklik's minimum essential medium-20 mM Hepes-2% BSA (JMEM-BSA). Endogenous bovine transferrin was removed from the HeLa cells by incubation for 10 min at 37° C. at a 5-fold dilution with JMEM-BSA. After centrifugation of the cells and removal of the supernatant, this procedure was repeated twice. The cells were then incubated for an additional 10 min in the presence of 10 mM NH$_4$Cl to inhibit the removal of iron from transferrin (Morgan (1981) *Biochim. Biophys. Acta* 642:119-134; Harding & Stahl (1983) *Biochem. Biophys. Res. Comm.* 113:650-658; Rao et al. (1983) *FEBS Lett.* 160:213-216; Klausner, et al. (1983) *J. Biol. Chem.* 2578:4715-4724; Mason et al. (1987) *Biochem J.* 245:103-109). Removal of the endogenous transferrin is somewhat superfluous since bovine transferrin has a very low affinity for human receptors and would not effectively compete with human transferrin in the binding studies (Penhallow, R. C. et al. (1986) *J. Cell. Physiol.* 128:251-260). For each diferric hTf sample to be tested, cell suspensions (300 μL containing ~2.2×10$^6$ cells) were added to eight different Omnivials containing between 3 and 80 pmol of radiolabeled diferric transferrin. An identical set of vials was set up containing a 100-fold excess of unlabeled Boehringer Mannheim diferric transferrin to determine the amount of nonspecific binding. After 30 min of incubation at 37° C. with gentle shaking, portions of the cell suspension (3×100 μL) were pipetted into microfuge tubes containing 0.9 mL of ice-cold JMEM-BSA over 300 μL of dibutyl phthalate and centrifuged for 2 min in a Beckman microfuge. The aqueous and organic phases were aspirated to just above the cell pellet. The bottom of the tube containing the cell pellet was released by a hot wire into a plastic tube (12×75 mm) and assayed for radioactivity. A second approach involved competing six different amounts (4-120 pmol) of each of the different hTf samples against a constant amount (6.4 pmol) of radioiodinated Boehringer Mannheim hTf. The program LIGAND was used to analyze the data from both types of experiment assuming a single class of binding sites in each case (Munson & Rodbard, (1980) *Anal. Biochem.* 107:220-239).

In order to test the functional integrity of the five different hTf samples, equilibrium binding studies were undertaken using two different approaches as discussed above. First, each hTf sample was radioiodinated, and direct binding to HeLa $S_3$ cells was measured in the presence and absence of a 100-fold excess of unlabeled Boehringer Mannheim $Fe_2$hTf. In all instances, the amount of nonspecific binding was very low, less than 5% of the specific binding. The data from the equilibrium binding experiment were analyzed by the nonlinear curve-fitting program of Munson and Rodbard to determine the affinity and binding site number for each TF (Munson & Rodbard, (1980) *Anal. Biochem.* 107:220-239). A typical data set is presented in Table 2. The results show that all of the transferrins bound with approximately the same affinity and to the same extent.

The second approach involved competing different amounts of each of the transferrins (unlabeled) against a constant amount of radioiodinated Boehringer Mannheim diferric hTf. The results of a typical data set from this approach are presented in Table IIIB. The two experiments shown were done on different days which probably accounts for the difference in the number of binding sites per cell observed. In many experiments over a number of years (Penhallow, R. C. et al. (1986) *J. Cell. Physiol.* 128:251-260), between 0.8 and $2 \times 10^6$ sites/cell have been found, which probably reflects the metabolic state of the cells. Binding of the recombinant Tf samples is indistinguishable from binding of the commercially available Tf samples.

TABLE 2[a]

| transferrin | $Kd^b$ (nM) | TF/cell[c] × $10^{-6}$ | $N^d$ |
|---|---|---|---|
| (A) Results of Equilibrium Binding Experiments in which Binding of Radioiodinated Diferric Transferrin to HeLa $S_3$ Cells Was Directly Measured | | | |
| recombinant glycosylated | 31.3 ± 3.6 | 2.09 ± 0.14 | 0.004 ± 0.003 |
| recombinant nonglycosylated | 23.4 ± 2.5 | 1.96 ± 0.13 | 0.013 ± 0.003 |
| Boehringer Mannheim | 17.8 ± 2.3 | 1.31 ± 0.08 | 0.019 ± 0.003 |
| Sigma | 19.9 ± 1.5 | 1.76 ± 0.14 | 0.009 ± 0.004 |
| Scipac | 22.5 ± 2.9 | 1.76 ± 0.09 | 0.008 ± 0.002 |
| (B) Results of Equilibrium Binding Experiments in which Six Different Amounts of Unlabeled Transferrin Were Competed against a Constant Amount of Boehringer Mannheim Radioiodinated Transferrin | | | |
| recombinant glycosylated | 22.6 ± 2.4 | 0.99 ± 0.03 | 0 |
| recombinant nonglycosylated | 19.8 ± 7.4 | 0.91 ± 0.07 | 0 |
| Boehringer Mannheim | 29.7 ± 1.6 | 1.00 ± 0.10 | 0.015 ± 0.006 |
| Sigma | 19.6 ± 9.7 | 0.79 ± 0.07 | 0.018 ± 0.005 |
| Scipac | 30.0 ± 1.8 | 1.04 ± 0.10 | 0.013 ± 0.006 |

[a] In (A), 7482 cpm bound (3.28 × $10^5$ TF/cell) in the absence of competitor. A total of 44 cpm bound in the presence of 100-fold excess of unlabeled competitor.
[b] In both experiments, $K_d$ denotes the apparent equilibrium binding constant.
[c] TF/cell denotes the number of TF molecules bound per cell.
[d] N denotes the ratio of nonspecifically bound to free transferrin.

EQUIVALENTS

Those skilled in the art will recognize, or be able to ascertain using no more than routine experimentation, numerous equivalents to the specific procedures described herein. Such equivalents are considered to be within the scope of this invention and are covered by the following claims.

---

What is claimed:

1. A nonserum supplement for cell culture medium comprising a homogenous preparation of recombinant, eukaryotically expressed, metal-binding full length human serum transferrin, wherein the transferrin has the mature peptide amino acid sequence set forth in SEQ ID NO:2, wherein at least one of Asn413 and Asn61 of SEQ ID NO:2 are mutated to an amino acid which does not allow glycosylation.

2. The nonserum supplement of claim 1, wherein the recombinant, eukaryotically expressed, human serum binds iron.

3. The nonserum supplement of claim 1, wherein the recombinant, eukaryotically expressed, human serum transferrin binds to a transferrin receptor.

4. The nonserum supplement of claim 1, wherein the recombinant, eukaryotically expressed, human serum transferrin is free of virus contamination.

5. A nonserum supplement for cell culture medium comprising a homogenous preparation of recombinant, eukaryotically expressed, carboxy-terminal lobe of human serum transferrin, comprising the amino acid sequence set forth as amino acid residues 343-679 of SEQ ID NO:2, herein at least one of Asn413 and Asn611 of SEQ ID NO:2 are mutated to an amino acid which does not allow glycosylation.

6. The nonserum supplement of claim 5, wherein the carboxy-terminal lobe of human serum transferrin binds iron.

7. The nonserum supplement of claim 5, wherein the carboxy-terminal lobe of human serum transferrin consists of amino acids 343-679 of SEQ ID NO:2.

8. The nonserum supplement of claim 1 or 5, wherein at least one of Asn413 and Asn611 of the human serum transferrin of SEQ ID NO:2 are mutated to an aspartic acid.

9. The nonserum supplement of claim 1 or 5, wherein Asn413 and Asn611 of the human serum transferrin are mutated.

10. The nonserum supplement of claim 9, wherein Asn413 and Asn611 are mutated to aspartic acid.

11. The nonserum supplement of claim 5, wherein the homogenous preparation is free of virus contamination.

12. The nonserum supplement of claim 1, wherein the human serum transferrin further comprises a mutation in at least one amino acid residue selected from the group consisting of Asp63, Gly65, Tyr95, Tyr188, His249, Asp392, Tyr426, Tyr517, and His585 of SEQ ID NO:2.

13. The nonserum supplement of claim 1, wherein the human serum transferrin comprises a mutation at Asp63 or Gly65 of the human serum transferrin of SEQ ID NO:2.

14. The nonserum supplement of claim 12 or 13, wherein Asp63 of the human serum transferrin of SEQ ID NO:2 is mutated.

15. The nonserum supplement of claim 14, wherein Asp63 is mutated to serine.

16. The nonserum supplement of claim 12 or 13, wherein Gly65 of the human serum transferrin of SEQ ID NO:2 is mutated.

17. The nonserum supplement of claim 16, wherein Gly65 is mutated to arginine.

18. The nonserum supplement of claim 1, wherein the human serum transferrin further comprises a mutation at Lys206 or His207 of SEQ ID NO:2, wherein the mutant has a stronger binding avidity for metal than wild-type human serum transferrin.

19. The nonserum supplement of claim 18, wherein Lys206 of the human serum transferrin of SEQ ID NO:2 is mutated.

20. The nonserum supplement of claim 19, wherein Lys206 is mutated to glutamine.

21. The nonserum supplement of claim 18, wherein His207 of the human serum transferrin of SEQ ID NO:2 is mutated.

22. The nonserum supplement of claim 21, wherein His207 is mutated to glutamic acid.

23. The nonserum supplement of claim 1, wherein the human serum transferrin further comprises a mutation at Lys206 and His207 of SEQ ID NO:2, wherein the mutant has a stronger binding avidity for metal than wild-type human serum transferrin.

24. The nonserum supplement of claim 23, wherein Lys206 is mutated to glutamine and His207 is mutated to glutamic acid.

\* \* \* \* \*

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 2327 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 31..2124

(ix) FEATURE:
      (A) NAME/KEY: mat_peptide
      (B) LOCATION: 88..2124

(xi) SEQUENCE DESCRIPTION: SEQ ID NO: 1:

```
TGTGCTCGCT GCTCAGCGCG CACCCGGAAG ATG AGG CTC GCC GTG GGA GCC CTG      54
                                Met Arg Leu Ala Val Gly Ala Leu
```

```
                          -19                -15
CTG GTC TGC GCC GTC CTG GGG CTG TGT CTG GCT GTC CCT GAT AAA ACT       102
Leu Val Cys Ala Val Leu Gly Leu Cys Leu Ala Val Pro Asp Lys Thr
    -10                 -5                   1                 5

GTG AGA TGG TGT GCA GTG TCG GAG CAT GAG GCC ACT AAG TGC CAG AGT       150
Val Arg Trp Cys Ala Val Ser Glu His Glu Ala Thr Lys Cys Gln Ser
            10                  15                  20

TTC CGC GAC CAT ATG AAA AGC GTC ATT CCA TCC GAT GGT CCC AGT GTT       198
Phe Arg Asp His Met Lys Ser Val Ile Pro Ser Asp Gly Pro Ser Val
                25                  30                  35

GCT TGT GTG AAG AAA GCC TCC TAC CTT GAT TGC ATC AGG GCC ATT GCG       246
Ala Cys Val Lys Lys Ala Ser Tyr Leu Asp Cys Ile Arg Ala Ile Ala
            40                  45                  50

GCA AAC GAA GCG GAT GCT GTG ACA CTG GAT GCA GGT TTG GTC TAT GAT       294
Ala Asn Glu Ala Asp Ala Val Thr Leu Asp Ala Gly Leu Val Tyr Asp
    55                  60                  65

GCT TAC TTG GCT CCC AAT AAC CTG AAG CCT GTG GTG GCA GAG TTC TAT       342
Ala Tyr Leu Ala Pro Asn Asn Leu Lys Pro Val Val Ala Glu Phe Tyr
70                  75                  80                  85

GGG TCA AAA GAG GAT CCA CAG ACT TTC TAT TAT GCT GTT GCT GTG GTG       390
Gly Ser Lys Glu Asp Pro Gln Thr Phe Tyr Tyr Ala Val Ala Val Val
                90                  95                  100

AAG AAG GAT AGT GGC TTC CAG ATG AAC CAG CTT CGA GGC AAG AAG TCC       438
Lys Lys Asp Ser Gly Phe Gln Met Asn Gln Leu Arg Gly Lys Lys Ser
            105                 110                 115

TGC CAC ACG GGT CTA GGC AGG TCC GCT GGG TGG AAC ATC CCC ATA GGC       486
Cys His Thr Gly Leu Gly Arg Ser Ala Gly Trp Asn Ile Pro Ile Gly
                120                 125                 130

TTA CTT TAC TGT GAC TTA CCT GAG CCA CGT AAA CCT CTT GAG AAA GCA       534
Leu Leu Tyr Cys Asp Leu Pro Glu Pro Arg Lys Pro Leu Glu Lys Ala
    135                 140                 145

GTG GCC AAT TTC TTC TCG GGC AGC TGT GCC CCT TGT GCG GAT GGG ACC       582
Val Ala Asn Phe Phe Ser Gly Ser Cys Ala Pro Cys Ala Asp Gly Thr
150                 155                 160                 165

GAC TTC CCC CAG CTG TGT CAA CTG TGT CCA GGG TGT GGC TGC TCC ACC       630
Asp Phe Pro Gln Leu Cys Gln Leu Cys Pro Gly Cys Gly Cys Ser Thr
                170                 175                 180

CTT AAC CAA TAC TTC GGC TAC TCG GGA GCC TTC AAG TGT CTG AAG GAT       678
Leu Asn Gln Tyr Phe Gly Tyr Ser Gly Ala Phe Lys Cys Leu Lys Asp
            185                 190                 195

GGT GCT GGG GAT GTG GCC TTT GTC AAG CAC TCG ACT ATA TTT GAG AAC       726
Gly Ala Gly Asp Val Ala Phe Val Lys His Ser Thr Ile Phe Glu Asn
                200                 205                 210

TTG GCA AAC AAG GCT GAC AGG GAC CAG TAT GAG CTG CTT TGC CTA GAC       774
Leu Ala Asn Lys Ala Asp Arg Asp Gln Tyr Glu Leu Leu Cys Leu Asp
    215                 220                 225

AAC ACC CGG AAG CCG GTA GAT GAA TAC AAG GAC TGC CAC TTG GCC CAG       822
Asn Thr Arg Lys Pro Val Asp Glu Tyr Lys Asp Cys His Leu Ala Gln
230                 235                 240                 245

GTC CCT TCT CAT ACC GTC GTG GCC CGA AGT ATG GGC GGC AAG GAG GAC       870
Val Pro Ser His Thr Val Val Ala Arg Ser Met Gly Gly Lys Glu Asp
                250                 255                 260

TTG ATC TGG GAG CTT CTC AAC CAG GCC CAG GAA CAT TTT GGC AAA GAC       918
Leu Ile Trp Glu Leu Leu Asn Gln Ala Gln Glu His Phe Gly Lys Asp
            265                 270                 275

AAA TCA AAA GAA TTC CAA CTA TTC AGC TCT CCT CAT GGG AAG GAC CTG       966
Lys Ser Lys Glu Phe Gln Leu Phe Ser Ser Pro His Gly Lys Asp Leu
                280                 285                 290

CTG TTT AAG GAC TCT GCC CAC GGG TTT TTA AAA GTC CCC CCA AGG ATG      1014
Leu Phe Lys Asp Ser Ala His Gly Phe Leu Lys Val Pro Pro Arg Met
```

```
                 295                 300                 305
GAT GCC AAG ATG TAC CTG GGC TAT GAG TAT GTC ACT GCC ATC CGG AAT   1062
Asp Ala Lys Met Tyr Leu Gly Tyr Glu Tyr Val Thr Ala Ile Arg Asn
310                 315                 320                 325

CTA CGG GAA GGC ACA TGC CCA GAA GCC CCA ACA GAT GAA TGC AAG CCT   1110
Leu Arg Glu Gly Thr Cys Pro Glu Ala Pro Thr Asp Glu Cys Lys Pro
                330                 335                 340

GTG AAG TGG TGT GCG CTG AGC CAC CAC GAG AGG CTC AAG TGT GAT GAG   1158
Val Lys Trp Cys Ala Leu Ser His His Glu Arg Leu Lys Cys Asp Glu
            345                 350                 355

TGG AGT GTT AAC AGT GTA GGG AAA ATA GAG TGT GTA TCA GCA GAG ACC   1206
Trp Ser Val Asn Ser Val Gly Lys Ile Glu Cys Val Ser Ala Glu Thr
        360                 365                 370

ACC GAA GAC TGC ATC GCC AAG ATC ATG AAT GGA GAA GCT GAT GCC ATG   1254
Thr Glu Asp Cys Ile Ala Lys Ile Met Asn Gly Glu Ala Asp Ala Met
    375                 380                 385

AGC TTG GAT GGA GGG TTT GTC TAC ATA GCG GGC AAG TGT GGT CTG GTG   1302
Ser Leu Asp Gly Gly Phe Val Tyr Ile Ala Gly Lys Cys Gly Leu Val
390                 395                 400                 405

CCT GTC TTG GCA GAA AAC TAC AAT AAG AGC GAT AAT TGT GAG GAT ACA   1350
Pro Val Leu Ala Glu Asn Tyr Asn Lys Ser Asp Asn Cys Glu Asp Thr
                410                 415                 420

CCA GAG GCA GGG TAT TTT GCT GTA GCA GTG GTG AAG AAA TCA GCT TCT   1398
Pro Glu Ala Gly Tyr Phe Ala Val Ala Val Val Lys Lys Ser Ala Ser
            425                 430                 435

GAC CTC ACC TGG GAC AAT CTG AAA GGC AAG AAG TCC TGC CAT ACG GCA   1446
Asp Leu Thr Trp Asp Asn Leu Lys Gly Lys Lys Ser Cys His Thr Ala
        440                 445                 450

GTT GGC AGA ACC GCT GGC TGG AAC ATC CCC ATG GGC CTG CTC TAC AAT   1494
Val Gly Arg Thr Ala Gly Trp Asn Ile Pro Met Gly Leu Leu Tyr Asn
    455                 460                 465

AAG ATC AAC CAC TGC AGA TTT GAT GAA TTT TTC AGT GAA GGT TGT GCC   1542
Lys Ile Asn His Cys Arg Phe Asp Glu Phe Phe Ser Glu Gly Cys Ala
470                 475                 480                 485

CCT GGG TCT AAG AAA GAC TCC AGT CTC TGT AAG CTG TGT ATG GGC TCA   1590
Pro Gly Ser Lys Lys Asp Ser Ser Leu Cys Lys Leu Cys Met Gly Ser
                490                 495                 500

GGC CTA AAC CTG TGT GAA CCC AAC AAC AAA GAG GGA TAC TAC GGC TAC   1638
Gly Leu Asn Leu Cys Glu Pro Asn Asn Lys Glu Gly Tyr Tyr Gly Tyr
            505                 510                 515

ACA GGC GCT TTC AGG TGT CTG GTT GAG AAG GGA GAT GTG GCC TTT GTG   1686
Thr Gly Ala Phe Arg Cys Leu Val Glu Lys Gly Asp Val Ala Phe Val
        520                 525                 530

AAA CAC CAG ACT GTC CCA CAG AAC ACT GGG GGA AAA AAC CCT GAT CCA   1734
Lys His Gln Thr Val Pro Gln Asn Thr Gly Gly Lys Asn Pro Asp Pro
    535                 540                 545

TGG GCT AAG AAT CTG AAT GAA AAA GAC TAT GAG TTG CTG TGC CTT GAT   1782
Trp Ala Lys Asn Leu Asn Glu Lys Asp Tyr Glu Leu Leu Cys Leu Asp
550                 555                 560                 565

GGT ACC AGG AAA CCT GTG GAG GAG TAT GCG AAC TGC CAC CTG GCC AGA   1830
Gly Thr Arg Lys Pro Val Glu Glu Tyr Ala Asn Cys His Leu Ala Arg
                570                 575                 580

GCC CCG AAT CAC GCT GTG GTC ACA CGG AAA GAT AAG GAA GCT TGC GTC   1878
Ala Pro Asn His Ala Val Val Thr Arg Lys Asp Lys Glu Ala Cys Val
            585                 590                 595

CAC AAG ATA TTA CGT CAA CAG CAG CAC CTA TTT GGA AGC AAC GTA ACT   1926
His Lys Ile Leu Arg Gln Gln Gln His Leu Phe Gly Ser Asn Val Thr
        600                 605                 610

GAC TGC TCG GGC AAC TTT TGT TTG TTC CGG TCG GAA ACC AAG GAC CTT   1974
Asp Cys Ser Gly Asn Phe Cys Leu Phe Arg Ser Glu Thr Lys Asp Leu
```

```
         615                 620                 625
CTG TTC AGA GAT GAC ACA GTA TGT TTG GCC AAA CTT CAT GAC AGA AAC         2022
Leu Phe Arg Asp Asp Thr Val Cys Leu Ala Lys Leu His Asp Arg Asn
630                 635                 640                 645

ACA TAT GAA AAA TAC TTA GGA GAA GAA TAT GTC AAG GCT GTT GGT AAC         2070
Thr Tyr Glu Lys Tyr Leu Gly Glu Glu Tyr Val Lys Ala Val Gly Asn
                    650                 655                 660

CTG AGA AAA TGC TCC ACC TCA TCA CTC CTG GAA GCC TGC ACT TTC CGT         2118
Leu Arg Lys Cys Ser Thr Ser Ser Leu Leu Glu Ala Cys Thr Phe Arg
                665                 670                 675

AGA CCT TAAAATCTCA GAGGTAGGGC TGCCACCAAG GTGAAGATGG GAACGCAGAT         2174
Arg Pro

GATCCATGAG TTTGCCCTGG TTTCACTGGC CCAAGTGGTT TGTGCTAACC ACGTCTGTCT      2234

TCACAGCTCT GTGTTGCCAT GTGTGCTGAA CAAAAATAA AAATTATTAT TGATTTTATA       2294

TTTCAAAAAA AAAAAAAAAA AAAAAAAAAA AAA                                    2327

(2) INFORMATION FOR SEQ ID NO: 2:

(i) SEQUENCE CHARACTERISTICS:
        (A) LENGTH: 698 amino acids
        (B) TYPE: amino acid
        (D) TOPOLOGY: linear (ii) MOLECULE TYPE: protein (xi) SEQUENCE DESCRIPTION: SEQ ID NO: 2:

Met Arg Leu Ala Val Gly Ala Leu Leu Val Cys Ala Val Leu Gly Leu
-19             -15                 -10                 -5

Cys Leu Ala Val Pro Asp Lys Thr Val Arg Trp Cys Ala Val Ser Glu
                 1                  5                  10

His Glu Ala Thr Lys Cys Gln Ser Phe Arg Asp His Met Lys Ser Val
        15                  20                  25

Ile Pro Ser Asp Gly Pro Ser Val Ala Cys Val Lys Lys Ala Ser Tyr
 30                  35                  40                  45

Leu Asp Cys Ile Arg Ala Ile Ala Ala Asn Glu Ala Asp Ala Val Thr
                 50                  55                  60

Leu Asp Ala Gly Leu Val Tyr Asp Ala Tyr Leu Ala Pro Asn Asn Leu
                 65                  70                  75

Lys Pro Val Val Ala Glu Phe Tyr Gly Ser Lys Glu Asp Pro Gln Thr
                 80                  85                  90

Phe Tyr Tyr Ala Val Ala Val Val Lys Lys Asp Ser Gly Phe Gln Met
 95                 100                 105

Asn Gln Leu Arg Gly Lys Lys Ser Cys His Thr Gly Leu Gly Arg Ser
110                 115                 120                 125

Ala Gly Trp Asn Ile Pro Ile Gly Leu Leu Tyr Cys Asp Leu Pro Glu
                130                 135                 140

Pro Arg Lys Pro Leu Glu Lys Ala Val Ala Asn Phe Phe Ser Gly Ser
                145                 150                 155

Cys Ala Pro Cys Ala Asp Gly Thr Asp Phe Pro Gln Leu Cys Gln Leu
                160                 165                 170

Cys Pro Gly Cys Gly Cys Ser Thr Leu Asn Gln Tyr Phe Gly Tyr Ser
                175                 180                 185

Gly Ala Phe Lys Cys Leu Lys Asp Gly Ala Gly Asp Val Ala Phe Val
190                 195                 200                 205

Lys His Ser Thr Ile Phe Glu Asn Leu Ala Asn Lys Ala Asp Arg Asp
                210                 215                 220
```

-continued

```
Gln Tyr Glu Leu Leu Cys Leu Asp Asn Thr Arg Lys Pro Val Asp Glu
                225                 230                 235

Tyr Lys Asp Cys His Leu Ala Gln Val Pro Ser His Thr Val Val Ala
            240                 245                 250

Arg Ser Met Gly Gly Lys Glu Asp Leu Ile Trp Glu Leu Leu Asn Gln
        255                 260                 265

Ala Gln Glu His Phe Gly Lys Asp Lys Ser Lys Glu Phe Gln Leu Phe
270                 275                 280                 285

Ser Ser Pro His Gly Lys Asp Leu Leu Phe Lys Asp Ser Ala His Gly
                290                 295                 300

Phe Leu Lys Val Pro Pro Arg Met Asp Ala Lys Met Tyr Leu Gly Tyr
            305                 310                 315

Glu Tyr Val Thr Ala Ile Arg Asn Leu Arg Glu Gly Thr Cys Pro Glu
        320                 325                 330

Ala Pro Thr Asp Glu Cys Lys Pro Val Lys Trp Cys Ala Leu Ser His
335                 340                 345

His Glu Arg Leu Lys Cys Asp Glu Trp Ser Val Asn Ser Val Gly Lys
350                 355                 360                 365

Ile Glu Cys Val Ser Ala Glu Thr Thr Glu Asp Cys Ile Ala Lys Ile
                370                 375                 380

Met Asn Gly Glu Ala Asp Ala Met Ser Leu Asp Gly Gly Phe Val Tyr
            385                 390                 395

Ile Ala Gly Lys Cys Gly Leu Val Pro Val Leu Ala Glu Asn Tyr Asn
        400                 405                 410

Lys Ser Asp Asn Cys Glu Asp Thr Pro Glu Ala Gly Tyr Phe Ala Val
415                 420                 425

Ala Val Val Lys Lys Ser Ala Ser Asp Leu Thr Trp Asp Asn Leu Lys
430                 435                 440                 445

Gly Lys Lys Ser Cys His Thr Ala Val Gly Arg Thr Ala Gly Trp Asn
                450                 455                 460

Ile Pro Met Gly Leu Leu Tyr Asn Lys Ile Asn His Cys Arg Phe Asp
            465                 470                 475

Glu Phe Phe Ser Glu Gly Cys Ala Pro Gly Ser Lys Lys Asp Ser Ser
        480                 485                 490

Leu Cys Lys Leu Cys Met Gly Ser Gly Leu Asn Leu Cys Glu Pro Asn
    495                 500                 505

Asn Lys Glu Gly Tyr Tyr Gly Tyr Thr Gly Ala Phe Arg Cys Leu Val
510                 515                 520                 525

Glu Lys Gly Asp Val Ala Phe Val Lys His Gln Thr Val Pro Gln Asn
                530                 535                 540

Thr Gly Gly Lys Asn Pro Asp Pro Trp Ala Lys Asn Leu Asn Glu Lys
            545                 550                 555

Asp Tyr Glu Leu Leu Cys Leu Asp Gly Thr Arg Lys Pro Val Glu Glu
        560                 565                 570

Tyr Ala Asn Cys His Leu Ala Arg Ala Pro Asn His Ala Val Val Thr
    575                 580                 585

Arg Lys Asp Lys Glu Ala Cys Val His Lys Ile Leu Arg Gln Gln Gln
590                 595                 600                 605

His Leu Phe Gly Ser Asn Val Thr Asp Cys Ser Gly Asn Phe Cys Leu
                610                 615                 620

Phe Arg Ser Glu Thr Lys Asp Leu Leu Phe Arg Asp Asp Thr Val Cys
            625                 630                 635

Leu Ala Lys Leu His Asp Arg Asn Thr Tyr Glu Lys Tyr Leu Gly Glu
        640                 645                 650
```

```
Glu Tyr Val Lys Ala Val Gly Asn Leu Arg Lys Cys Ser Thr Ser Ser
    655                 660                 665

Leu Leu Glu Ala Cys Thr Phe Arg Arg Pro
670                 675
```

(2) INFORMATION FOR SEQ ID NO: 3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

GCAGAAAACT ACGATAAGAG CGATAAT                       27

(2) INFORMATION FOR SEQ ID NO: 4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

CTATTTGGAA GCGACGTAAC TGACTGC                       27

(2) INFORMATION FOR SEQ ID NO: 5:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 5:

```
Val Pro Asp Lys Thr Val Arg Trp Cys Ala Val Ser
1               5                   10
```

(2) INFORMATION FOR SEQ ID NO: 6:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 6:

```
Val Pro Asp Lys Thr Val Arg Trp Xaa Ala Val Ser
1               5                   10
```

(2) INFORMATION FOR SEQ ID NO: 7:

(i) SEQUENCE CHARACTERISTICS:
        (A) LENGTH: 6 amino acids
        (B) TYPE: amino acid
        (D) TOPOLOGY: linear (ii) MOLECULE TYPE: peptide

```
    (v) FRAGMENT TYPE: internal (xi) SEQUENCE DESCRIPTION: SEQ ID NO: 7:

Val Pro Asp Lys Thr Val
1               5
```